(12) United States Patent
Gelfand

(10) Patent No.: US 8,143,387 B2
(45) Date of Patent: Mar. 27, 2012

(54) ENGINEERED ANTIBODY-STRESS PROTEIN FUSIONS

(75) Inventor: Jeffrey A. Gelfand, Cambridge, MA (US)

(73) Assignee: The General Hospital Corporation, Charlestown, MA (US)

(*) Notice: Subject to any disclaimer, the term of this patent is extended or adjusted under 35 U.S.C. 154(b) by 0 days.

(21) Appl. No.: 12/783,186

(22) Filed: May 19, 2010

(65) Prior Publication Data

US 2010/0255539 A1  Oct. 7, 2010

Related U.S. Application Data

(63) Continuation of application No. 12/185,631, filed on Aug. 4, 2008, now Pat. No. 7,749,501, which is a continuation-in-part of application No. PCT/US2007/061554, filed on Feb. 2, 2007.

(60) Provisional application No. 60/764,620, filed on Feb. 2, 2006.

(51) Int. Cl.
  *C07H 21/04* (2006.01)
  *C07H 21/02* (2006.01)
  *A61K 39/00* (2006.01)

(52) U.S. Cl. ............... 536/23.7; 535/23.1; 535/23.4; 535/23.5; 424/130.1; 424/133.1; 424/134.1; 424/135.7; 424/136.1

(58) Field of Classification Search .............. 536/23.1, 536/23.4, 23.5, 23.7; 424/130.1, 133.1, 134.1, 424/135.1, 136.1
See application file for complete search history.

(56) References Cited

U.S. PATENT DOCUMENTS

| 6,338,952 | B1 | 1/2002 | Young |
| 7,189,396 | B1 | 3/2007 | Weisbart |

FOREIGN PATENT DOCUMENTS

| WO | WO-03/068822 | 8/2003 |
| WO | WO-03/091266 | 11/2003 |
| WO | WO-03/092624 | 11/2003 |

OTHER PUBLICATIONS

Cochlovius et al., "Cure of Burkitt's Lymphoma in Severe Combined Immunodeficiency Mice by T Cells, Tetravalent CD3 × CD19 Tandem Diabody, and CD28 Costimulation," Cancer Research, 60:4336-4341 (2000).
Hansen et al., "Antibody-mediated Hsp70 protein therapy," Brain Research, 1088:187-196 (2006).
Hansen et al., "Antibody-Mediated Transduction of Therapeutic Proteins into Living Cells," The Scientific World Journal, 5:782-788 (2005).
Supplementary European Search Report dated Sep. 14, 2010 from EP 07 81 1793.

*Primary Examiner* — Rodney P. Swartz
(74) *Attorney, Agent, or Firm* — Foley Hoag LLP

(57) ABSTRACT

Provided are fusion polypeptides comprising an engineered antibody and a stress protein that bind to antigens with high affinity, are highly immunogenic, exhibit MHC class I priming and are able to be produced in non-mammalian cells, such as *E. coli*.

20 Claims, 9 Drawing Sheets

Fig. 2

SEQ ID NO: 1 Chaperone protein dnaK (Heat shock protein 70) from *Mycobacterium tuberculosis* (P0A5B9, GI:61222666)

```
  1  maravgidlg ttnsvvsvle ggdpvvvans egsrttpsiv afarngevlv gqpaknqavt
 61  nvdrtvrsvk rhmgsdwsie idgkkytape isarilmklk rdaeaylged itdavittpa
121  yfndaqrqat kdagqiagln vlrivnepta aalaygldkg ekeqrilvfd lgggtfdvsl
181  leigegvvev ratsgdnhlg gddwdqrvvd wlvdkfkgts gidltkdkma mqrlreaaek
241  akielsssqs tsinlpyitv dadknplfld eqltraefqr itqdlldrtr kpfqsviadt
301  gisvseidhv vlvggstrmp avtdlvkelt ggkepnkgvn pdevvavgaa lqagvlkgev
361  kdvllldvtp lslgietkgg vmtrliernt tiptkrsetf ttaddnqpsv qiqvyqgere
421  iaahnkllgs feltgippap rgipqievtf didangivhv takdkgtgke ntiriqegsg
481  lskedidrmi kdaeahaeed rkrreeadvr nqaetlvyqt ekfvkeqrea eggskvpedt
541  lnkvdaavae akaalggsdi saiksamekl gqesqalgqa iyeaaqaasq atgaahpgge
601  pggahpgsad dvvdaevvdd greak
```

SEQ ID NO: 2 Chaperone protein dnaK (Heat shock protein 70) from *Mycobacterium bovis* (NP_854021.1 GI:31791528)

```
  1  maravgidlg ttnsvvsvle ggdpvvvans egsrttpsiv afarngevlv gqpaknqavt
 61  nvdrtvrsvk rhmgsdwsie idgkkytape isarilmklk rdaeaylged itdavittpa
121  yfndaqrqat kdagqiagln vlrivnepta aalaygldkg ekeqrilvfd lgggtfdvsl
181  leigegvvev ratsgdnhlg gddwdqrvvd wlvdkfkgts gidltkdkma mqrlreaaek
241  akielsssqs tsinlpyitv dadknplfld eqltraefqr itqdlldrtr kpfqsviadt
301  gisvseidhv vlvggstrmp avtdlvkelt ggkepnkgvn pdevvavgaa lqagvlkgev
361  kdvllldvtp lslgietkgg vmtrliernt tiptkrsetf ttaddnqpsv qiqvyqgere
421  iaahnkllgs feltgippap rgipqievtf didangivhv takdkgtgke ntiriqegsg
481  lskedidrmi kdaeahaeed rkrreeadvr nqaetlvyqt ekfvkeqrea eggskvpedt
541  lnkvdaavae akaalggsdi saiksamekl gqesqalgqa iyeaaqaasq atgaahpgge
601  pggahpgsad dvvdaevvdd greak
```

Fig. 4

| Adsorbed | MISR-hsp70 fuse | MISR peptide | Hsp70 |
|---|---|---|---|
| Mabs clone ng/ml | | MISR B10 | |
| 1000 | 2.033 | 2.017 | 0.097 |
| 333 | 1.864 | 1.884 | 0.061 |
| 111 | 1.499 | 1.504 | 0.058 |
| 37 | 1.051 | 1.005 | 0.057 |
| 12.3 | 0.616 | 0.521 | 0.060 |
| 4.1 | 0.431 | 0.229 | 0.059 |
| 1.3 | 0.216 | 0.069 | 0.058 |
| 0 | 0.199 | 0.054 | 0.078 |

| Adsorbed | MISR–hsp70 fuse | MISR peptide | Hsp70 |
|---|---|---|---|
| Mabs clone Ng/ml | | MISR E4 | |
| 1000 | 2.073 | 2.031 | 0.112 |
| 333 | 2.037 | 2.172 | 0.064 |
| 111 | 1.512 | 2.178 | 0.063 |
| 37 | 0.838 | 1.860 | 0.062 |
| 12.3 | 0.437 | 1.069 | 0.065 |
| 4.1 | 0.322 | 0.495 | 0.064 |
| 1.3 | 0.169 | 0.116 | 0.063 |
| 0 | 0.082 | 0.061 | 0.078 |

Fig. 4 (cont)

| Adsorbed       | MISR-hsp70 fuse | MISR peptide | Hsp70 |
|----------------|-----------------|--------------|-------|
| Mabs clone Ng/ml |               | MISR E10     |       |
| 1000           | 1.827           | 2.068        | 0.122 |
| 333            | 1.564           | 2.029        | 0.071 |
| 111            | 1.206           | 1.783        | 0.070 |
| 37             | 0.818           | 1.380        | 0.069 |
| 12.3           | 0.503           | 0.915        | 0.072 |
| 4.1            | 0.352           | 0.467        | 0.070 |
| 1.3            | 0.170           | 0.124        | 0.071 |
| 0              | 0.171           | 0.061        | 0.090 |

| Adsorbed       | MISR-hsp70 fuse | MISR peptide | Hsp70 |
|----------------|-----------------|--------------|-------|
| Mabs clone Ng/ml |               | MISR G7      |       |
| 1000           | 1.956           | 1.936        | 0.146 |
| 333            | 1.753           | 1.584        | 0.106 |
| 111            | 1.306           | 1.166        | 0.098 |
| 37             | 0.805           | 0.684        | 0.099 |
| 12.3           | 0.471           | 0.301        | 0.104 |
| 4.1            | 0.322           | 0.117        | 0.101 |
| 1.3            | 0.163           | 0.055        | 0.097 |
| 0              | 0.180           | 0.062        | 0.110 |

MTBhsp70SpL fusion + MAb

Figure 10

SEQUENCE LISTING

<160> NUMBER OF SEQ ID NOS: 3

<210> SEQ ID NO 1
<211> LENGTH: 625
<212> TYPE: PRT
<213> ORGANISM: Mycobacterium tuberculosis

<400> SEQUENCE: 1

-continued

```
Met Ala Arg Ala Val Gly Ile Asp Leu Gly Thr Thr Asn Ser Val Val
 1               5                  10                  15

Ser Val Leu Glu Gly Gly Asp Pro Val Val Ala Asn Ser Glu Gly Gly
                20                  25                  30

Ser Arg Thr Thr Pro Ser Ile Val Ala Phe Ala Arg Asn Gly Glu Val
            35                  40                  45

Leu Val Gly Gln Pro Ala Lys Asn Gln Ala Val Thr Asn Val Asp Arg
     50                  55                  60

Thr Val Arg Ser Val Lys Arg His Met Gly Ser Asp Trp Ser Ile Glu
 65                  70                  75                  80

Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
            100                 105                 110

Asp Ala Val Ile Thr Thr Pro Ala Tyr Phe Asn Asp Ala Gln Arg Gln
            115                 120                 125

Ala Thr Lys Asp Ala Gly Gln Ile Ala Gly Leu Asn Val Leu Arg Ile
    130                 135                 140

Val Asn Glu Pro Thr Ala Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
    195                 200                 205

Val Asp Trp Leu Val Asp Lys Phe Lys Gly Thr Ser Gly Ile Asp Leu
    210                 215                 220

Thr Lys Asp Lys Met Ala Met Gln Arg Leu Arg Glu Ala Ala Glu Lys
225                 230                 235                 240

Ala Lys Ile Glu Leu Ser Ser Ser Gln Ser Thr Ser Ile Asn Leu Pro
                245                 250                 255

Tyr Ile Thr Val Asp Ala Asp Lys Asn Pro Leu Phe Leu Asp Glu Gln
            260                 265                 270

Leu Thr Arg Ala Glu Phe Gln Arg Ile Thr Gln Asp Leu Leu Asp Arg
    275                 280                 285

Thr Arg Lys Pro Phe Gln Ser Val Ile Ala Asp Thr Gly Ile Ser Val
    290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Lys Glu Pro Asn
                325                 330                 335

Lys Gly Val Asn Pro Asp Glu Val Val Ala Val Gly Ala Ala Leu Gln
            340                 345                 350

Ala Gly Val Leu Lys Gly Glu Val Lys Asp Val Leu Leu Leu Asp Val
    355                 360                 365

Thr Pro Leu Ser Leu Gly Ile Glu Thr Lys Gly Gly Val Met Thr Arg
    370                 375                 380

Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
            405                 410                 415

Gly Glu Arg Glu Ile Ala Ala His Asn Lys Leu Leu Gly Ser Phe Glu
```

```
                    420                 425                 430
Leu Thr Gly Ile Pro Pro Ala Pro Arg Gly Ile Pro Gln Ile Glu Val
            435                 440                 445
Thr Phe Asp Ile Asp Ala Asn Gly Ile Val His Val Thr Ala Lys Asp
        450                 455                 460
Lys Gly Thr Gly Lys Glu Asn Thr Ile Arg Ile Gln Glu Gly Ser Gly
465                 470                 475                 480
Leu Ser Lys Glu Asp Ile Asp Arg Met Ile Lys Asp Ala Glu Ala His
            485                 490                 495
Ala Glu Glu Asp Arg Lys Arg Glu Glu Ala Asp Val Arg Asn Gln
        500                 505                 510
Ala Glu Thr Leu Val Tyr Gln Thr Glu Lys Phe Val Lys Glu Gln Arg
        515                 520                 525
Glu Ala Glu Gly Gly Ser Lys Val Pro Glu Asp Thr Leu Asn Lys Val
        530                 535                 540
Asp Ala Ala Val Ala Glu Ala Lys Ala Ala Leu Gly Gly Ser Asp Ile
545                 550                 555                 560
Ser Ala Ile Lys Ser Ala Met Glu Lys Leu Gly Gln Glu Ser Gln Ala
            565                 570                 575
Leu Gly Gln Ala Ile Tyr Glu Ala Ala Gln Ala Ala Ser Gln Ala Thr
        580                 585                 590
Gly Ala Ala His Pro Gly Gly Glu Pro Gly Gly Ala His Pro Gly Ser
            595                 600                 605
Ala Asp Asp Val Val Asp Ala Glu Val Val Asp Gly Arg Glu Ala
        610                 615                 620
Lys
625

<210> SEQ ID NO 2
<211> LENGTH: 625
<212> TYPE: PRT
<213> ORGANISM: Mycobacterium bovis

<400> SEQUENCE: 2

Met Ala Arg Ala Val Gly Ile Asp Leu Gly Thr Thr Asn Ser Val Val
1               5                   10                  15
Ser Val Leu Glu Gly Gly Asp Pro Val Val Ala Asn Ser Glu Gly
            20                  25                  30
Ser Arg Thr Thr Pro Ser Ile Val Ala Phe Ala Arg Asn Gly Glu Val
        35                  40                  45
Leu Val Gly Gln Pro Ala Lys Asn Gln Ala Val Thr Asn Val Asp Arg
    50                  55                  60
Thr Val Arg Ser Val Lys Arg His Met Gly Ser Asp Trp Ser Ile Glu
65                  70                  75                  80
Ile Asp Gly Lys Lys Tyr Thr Ala Pro Glu Ile Ser Ala Arg Ile Leu
            85                  90                  95
Met Lys Leu Lys Arg Asp Ala Glu Ala Tyr Leu Gly Glu Asp Ile Thr
        100                 105                 110
Asp Ala Val Ile Thr Thr Pro Ala Tyr Phe Asn Asp Ala Gln Arg Gln
    115                 120                 125
Ala Thr Lys Asp Ala Gly Gln Ile Ala Gly Leu Asn Val Leu Arg Ile
130                 135                 140
Val Asn Glu Pro Thr Ala Ala Ala Leu Ala Tyr Gly Leu Asp Lys Gly
145                 150                 155                 160
Glu Lys Glu Gln Arg Ile Leu Val Phe Asp Leu Gly Gly Gly Thr Phe
```

```
                        165                 170                 175
Asp Val Ser Leu Leu Glu Ile Gly Glu Gly Val Glu Val Arg Ala
            180                 185                 190
Thr Ser Gly Asp Asn His Leu Gly Gly Asp Asp Trp Asp Gln Arg Val
        195                 200                 205
Val Asp Trp Leu Val Asp Lys Phe Lys Gly Thr Ser Gly Ile Asp Leu
    210                 215                 220
Thr Lys Asp Lys Met Ala Met Gln Arg Leu Arg Glu Ala Ala Glu Lys
225                 230                 235                 240
Ala Lys Ile Glu Leu Ser Ser Ser Gln Ser Thr Ser Ile Asn Leu Pro
                245                 250                 255
Tyr Ile Thr Val Asp Ala Asp Lys Asn Pro Leu Phe Leu Asp Glu Gln
            260                 265                 270
Leu Thr Arg Ala Glu Phe Gln Arg Ile Thr Gln Asp Leu Leu Asp Arg
        275                 280                 285
Thr Arg Lys Pro Phe Gln Ser Val Ile Ala Asp Thr Gly Ile Ser Val
    290                 295                 300
Ser Glu Ile Asp His Val Val Leu Val Gly Gly Ser Thr Arg Met Pro
305                 310                 315                 320
Ala Val Thr Asp Leu Val Lys Glu Leu Thr Gly Gly Lys Glu Pro Asn
                325                 330                 335
Lys Gly Val Asn Pro Asp Glu Val Val Ala Val Gly Ala Ala Leu Gln
            340                 345                 350
Ala Gly Val Leu Lys Gly Glu Val Lys Asp Val Leu Leu Leu Asp Val
        355                 360                 365
Thr Pro Leu Ser Leu Gly Ile Glu Thr Lys Gly Gly Val Met Thr Arg
    370                 375                 380
Leu Ile Glu Arg Asn Thr Thr Ile Pro Thr Lys Arg Ser Glu Thr Phe
385                 390                 395                 400
Thr Thr Ala Asp Asp Asn Gln Pro Ser Val Gln Ile Gln Val Tyr Gln
                405                 410                 415
Gly Glu Arg Glu Ile Ala Ala His Asn Lys Leu Leu Gly Ser Phe Glu
            420                 425                 430
Leu Thr Gly Ile Pro Pro Ala Pro Arg Gly Ile Pro Gln Ile Glu Val
        435                 440                 445
Thr Phe Asp Ile Asp Ala Asn Gly Ile Val His Val Thr Ala Lys Asp
    450                 455                 460
Lys Gly Thr Gly Lys Glu Asn Thr Ile Arg Ile Gln Glu Gly Ser Gly
465                 470                 475                 480
Leu Ser Lys Glu Asp Ile Asp Arg Met Ile Lys Asp Ala Glu Ala His
                485                 490                 495
Ala Glu Glu Asp Arg Lys Arg Arg Glu Glu Ala Asp Val Arg Asn Gln
            500                 505                 510
Ala Glu Thr Leu Val Tyr Gln Thr Glu Lys Phe Val Lys Glu Gln Arg
        515                 520                 525
Glu Ala Glu Gly Gly Ser Lys Val Pro Glu Asp Thr Leu Asn Lys Val
    530                 535                 540
Asp Ala Ala Val Ala Glu Ala Lys Ala Ala Leu Gly Gly Ser Asp Ile
545                 550                 555                 560
Ser Ala Ile Lys Ser Ala Met Glu Lys Leu Gly Gln Glu Ser Gln Ala
                565                 570                 575
Leu Gly Gln Ala Ile Tyr Glu Ala Ala Gln Ala Ala Ser Gln Ala Thr
            580                 585                 590
```

```
Gly Ala Ala His Pro Gly Gly Glu Pro Gly Gly Ala His Pro Gly Ser
            595                 600                 605
Ala Asp Asp Val Val Asp Ala Glu Val Val Asp Asp Gly Arg Glu Ala
        610                 615                 620
Lys
625

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Ala Asn Tyr Ser His Leu Pro Pro Ser Gly Asn Arg Gly
 1               5                  10
```

ENGINEERED ANTIBODY-STRESS PROTEIN FUSIONS

RELATED APPLICATIONS

This application is a continuation of U.S. application Ser. No. 12/185,631, filed on Aug. 4, 2008, now U.S. Pat. No. 7,749,501, issued Jul. 6, 2010, which is a continuation-in-part application of PCT/US07/061,554, filed Feb. 2, 2007, which claims priority to U.S. Application Ser. No. 60/764,620 filed Feb. 2, 2006. The contents of each of these applications are expressly incorporated herein by reference.

GOVERNMENT SUPPORT

The subject invention was made in part with government support under Department of State Grant S-LMAQM-04-GR-164, awarded by the Accelerated Drug and Vaccine Development with Former Soviet Union Institutions in Support of the U.S. Department of State BioIndustry Initiative. Accordingly, the U.S. Government has certain rights in this invention.

BACKGROUND OF THE INVENTION

Classical monoclonal antibodies are currently produced in mammalian cells. Drawbacks of this method of production include the difficulty of producing and selecting appropriate clones, and the expense of culturing mammalian cells. The "next generation" of monoclonal antibodies are being engineered in *E. coli*. Recently, microbial expression of $V_H$ and $V_L$ domains tethered together by polypeptide linkers has created the capability of generating engineered "mini-antibodies." These mini-bodies can be generated in *E. coli* in a virtually combinatorial fashion. These artificially created Fab or single chain Fv (scFv) can be linked together to form multimers, e.g., diabodies, triabodies and tetrabodies. Although they are capable of binding to antigens with almost antibody-like efficiency, these engineered, Fc deficient mini-antibodies lack the ability to interact with antigen presenting cells and are poorly immunogenic.

Existing solutions to the lack of immunogenicity of engineered antibodies involve directing one of the antigen binding sites to bind directly with immune cells. This brings them in apposition, but does not result in the same MHC class I priming as would be observed for a monoclonal antibody.

SUMMARY OF THE INVENTION

In one aspect, provided are fusions of an engineered antibody, such as a Fab or scFv, with a stress protein, such as HSP70. Stress proteins are very efficient at presenting antigens to antigen presenting cells and provoking a T cell response. They have been particularly effective at eliciting cell mediated immune and humoral immune responses by this pathway.

Thus, the fusion molecules bind to antigens with high affinity, are highly immunogenic, exhibit MHC class I priming, provoke a T cell response and are able to be produced in non-mammalian systems such as *E. coli*. The fusion molecules are thus suitable for use as highly immunogenic vaccines for the prevention or treatment of infectious, inflammatory, autoimmune, or malignant disease.

Accordingly, provided are fusion polypeptides comprising at least one engineered antibody and at least one stress protein. These engineered antibodies comprising the fusion polypeptides may be multivalent, i.e., they may be bivalent, trivalent, tetravalent, pentavalent, etc. Further, they may be monospecific or multispecific.

Also provided are nucleic acids and vectors encoding the engineered antibody-stress protein fusion polypeptides, host cells comprising the nucleic acids and vectors and methods for producing the engineered antibody-stress protein fusion polypeptides. Antigen combining sites or engineered antibody fragments can be created quickly and with high affinity, and may be inexpensively fused to a stress protein.

Further provided are pharmaceutical and vaccine compositions comprising the subject engineered antibody-stress protein fusion polypeptides. Such compositions may further comprise an adjuvant or other agent. Also provided are methods of preventing or treating infectious, inflammatory, autoimmune or malignant disease in a patient comprising administering to a patient in need thereof, an effective amount of any one of the aforementioned compositions.

Kits for the practice of the methods are also described herein.

Other features and advantages will be apparent from the following detailed description, and from the claims.

BRIEF DESCRIPTION OF THE DRAWINGS

FIG. 2 depicts the full-length polypeptide sequences of HSP70 from *Mycobacterium tuberculosis* HSP70 and *Mycobacterium bovis* HSP70, respectively.

FIG. 4. $OD_{450nm}$. The antigens for coating were taken at the concentration 1 µg/ml in PBS. The primary antibodies were incubated in PBS with 0.2% BSA and 0.05% Tween 20 at serial dilutions. Secondary anti-mouse antibodies conjugated with HRP were used.

Figure 10:
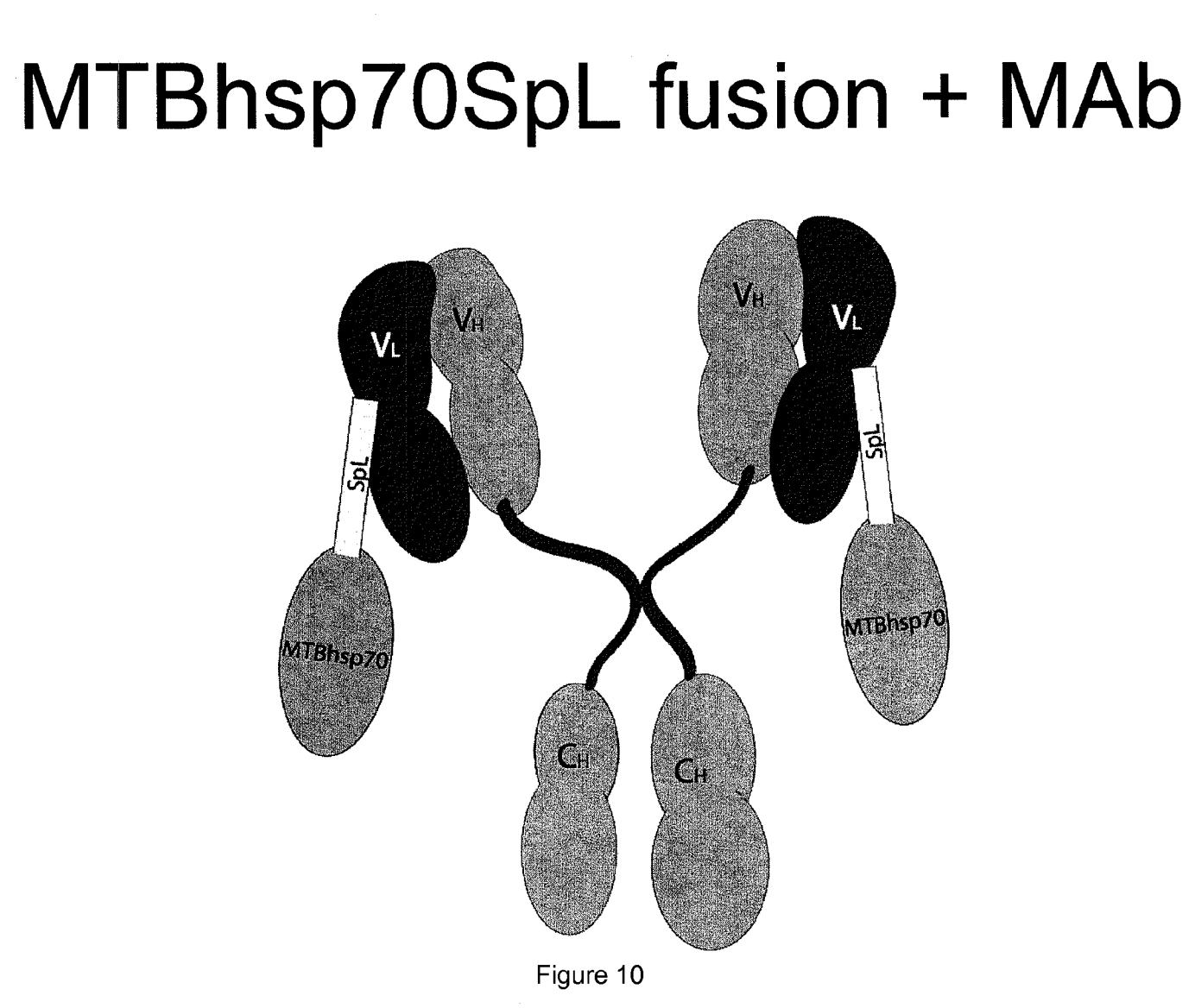

FIG. 10 shows an MTB HSP 70 fusion with an antibody.

DETAILED DESCRIPTION

Figure 1:
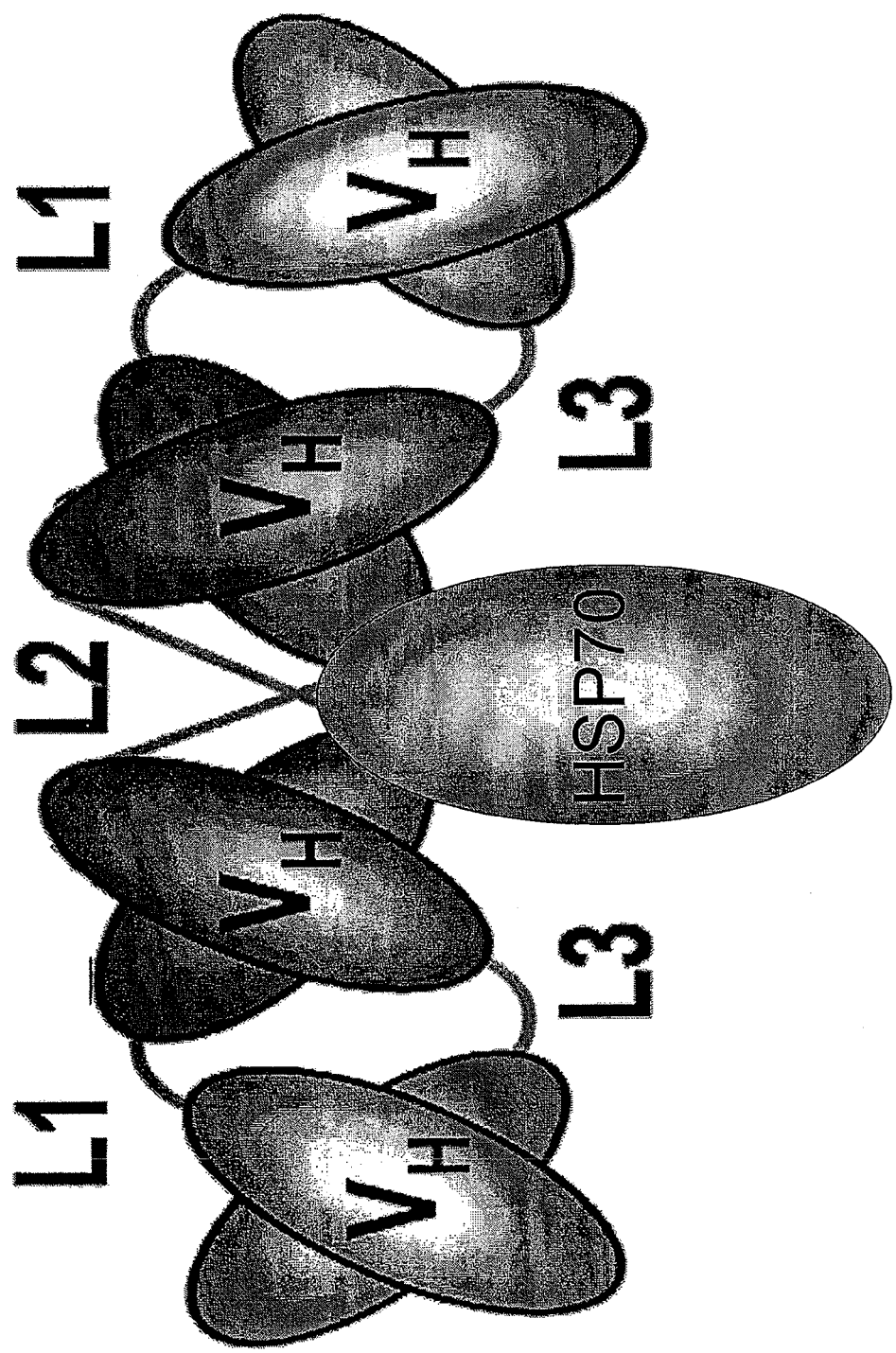
FIG. 1 depicts an exemplary engineered antibody-stress protein fusion polypeptide comprising a tetravalent Tandab (engineered antibody) and HSP70 (stress protein).

For convenience, before further description of the present invention, certain terms employed in the specification, examples and appended claims are defined here.

The singular forms "a", "an", and "the" include plural references unless the context clearly dictates otherwise.

The term "administering" includes any method of delivery of a compound of the present invention, including but not limited to, a pharmaceutical composition or therapeutic agent, into a subject's system or to a particular region in or on a subject. The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration. "Parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of the foregoing. The names of the natural amino acids are abbreviated herein in accordance with the recommendations of IUPAC-IUB.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The terms "comprise" and "comprising" is used in the inclusive, open sense, meaning that additional elements may be included.

The term "effective amount" refers to that amount of a compound, material, or composition which is sufficient to effect a desired result. An effective amount of a compound can be administered in one or more administrations.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

A "fusion protein" or "fusion polypeptide" refers to a hybrid polypeptide which comprises polypeptide portions from at least two different polypeptides. The portions may be from proteins of the same organism, in which case the fusion protein is said to be "intraspecies", "intragenic", etc. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. A first polypeptide may be fused to the N-terminus, the C-terminus, or the N- and C-terminus of a second polypeptide. Furthermore, a first polypeptide may be inserted within the sequence of a second polypeptide.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')$_2$ fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

"Host cell" refers to a cell that may be transduced with a specified transfer vector. The cell is optionally selected from in vitro cells such as those derived from cell culture, ex vivo cells, such as those derived from an organism, and in vivo cells, such as those in an organism. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "including" is used herein to mean "including but not limited to". "Including" and "including but not limited to" are used interchangeably.

The term "immunogenic" refers to the ability of a substance to elicit an immune response. An "immunogenic composition" or "immunogenic substance" is a composition or substance which elicits an immune response. An "immune response" refers to the reaction of a subject to the presence of an antigen, which may include at least one of the following: making antibodies, developing immunity, developing hypersensitivity to the antigen, and developing tolerance.

The term "isolated polypeptide" refers to a polypeptide, which may be prepared from recombinant DNA or RNA, or be of synthetic origin, some combination thereof, or which may be a naturally-occurring polypeptide, which (1) is not associated with proteins with which it is normally associated in nature, (2) is isolated from the cell in which it normally occurs, (3) is essentially free of other proteins from the same cellular source, (4) is expressed by a cell from a different species, or (5) does not occur in nature.

The term "isolated nucleic acid" refers to a polynucleotide of genomic, cDNA, synthetic, or natural origin or some combination thereof, which (1) is not associated with the cell in which the "isolated nucleic acid" is found in nature, or (2) is operably linked to a polynucleotide to which it is not linked in nature.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

"Protein" (if single-chain), "polypeptide" and "peptide" are used interchangeably herein when referring to a gene product, e.g., as may be encoded by a coding sequence. When referring to "polypeptide" herein, a person of skill in the art will recognize that a protein can be used instead, unless the context clearly indicates otherwise. A "protein" may also refer to an association of one or more polypeptides. By "gene product" is meant a molecule that is produced as a result of transcription of a gene. Gene products include RNA molecules transcribed from a gene, as well as proteins translated from such transcripts.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

A "patient" or "subject" or "host" refers to either a human or non-human animal.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

A "pharmaceutically-acceptable salt" refers to the relatively non-toxic, inorganic and organic acid addition salts of compounds.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

As used herein, a "stress protein," also known as a "heat shock protein" or "Hsp," is a protein that is encoded by a stress gene, and is therefore typically produced in significantly greater amounts upon the contact or exposure of the stressor to the organism. The term "stress protein" as used herein is intended to include such portions and peptides of a stress protein. A "stress gene," also known as "heat shock gene", as used herein, refers a gene that is activated or otherwise detectably upregulated due to the contact or exposure of an organism (containing the gene) to a stressor, such as heat shock, hypoxia, glucose deprivation, heavy metal salts, inhibitors of energy metabolism and electron transport, and protein denaturants, or to certain benzoquinone ansamycins. Nover, L., Heat Shock Response, CRC Press, Inc., Boca Raton, Fla. (1991). "Stress gene" also includes homologous genes within known stress gene families, such as certain genes within the Hsp70 and Hsp90 stress gene families, even though such homologous genes are not themselves induced by a stressor. Each of the terms stress gene and stress protein as used in the present specification may be inclusive of the other, unless the context indicates otherwise.

"Treating" a disease in a subject or "treating" a subject having a disease refers to subjecting the subject to a pharmaceutical treatment, e.g., the administration of a drug, such that the extent of the disease is decreased or prevented. Treatment includes (but is not limited to) administration of a composition, such as a pharmaceutical composition, and may be performed either prophylactically, or subsequent to the initiation of a pathologic event.

The term "vaccine" refers to a substance that elicits an immune response and also confers protective immunity upon a subject.

"Vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops, which, in their vector form are not bound to the chromosome. In the present specification, "plasmid" and "vector" are used interchangeably as the plasmid is the most commonly used form of vector. However, as will be appreciated by those skilled in the art, the invention is intended to include such other forms of expression vectors which serve equivalent functions and which become subsequently known in the art.

1. Engineered Antibody-Stress Protein Fusion Polypeptides

Provided are fusion polypeptides comprising an engineered antibody and a stress protein. The engineered antibody may comprise for example, at least one scFv, at least one Fab fragment, at least one Fv fragment, etc. It may be monovalent or it may be multivalent. In embodiments wherein the engineered antibody is multivalent, it may be bivalent, trivalent, tetravalent, etc. The multivalent antibodies may be monospecific or multispecific, e.g., bispecific, trispecific, tetraspecific, etc. The multivalent antibodies may be in any form, such as a diabody, triabody, tetrabody, etc. In certain embodiments, the engineered antibody is a Tandab. The stress protein may comprise any stress protein. In certain embodiments, the stress protein comprises HSP70, for example, *Mycobacterium tuberculosis* HSP70 or *Mycobacterium bovis* HSP70. The full-length polypeptide sequences of *Mycobacterium tuberculosis* HSP70 and *Mycobacterium bovis* HSP70 are depicted in FIG. 2 as SEQ ID NOs: 1 and 2, respectively.

Further detail about engineered antibodies and stress proteins which may be incorporated into the subject fusion polypeptides is provided below.

A. Engineered Antibodies

Natural antibodies are themselves dimers, and thus, bivalent. If two hybridoma cells producing different antibodies are artificially fused, some of the antibodies produced by the hybrid hybridoma are composed of two monomers with different specificities. Such bispecific antibodies can also be produced by chemically conjugating two antibodies. Natural antibodies and their bispecific derivatives are relatively large and expensive to produce. The constant domains of mouse antibodies are also a major cause of the human anti-mouse antibody (HAMA) response, which prevents their extensive use as therapeutic agents. They can also give rise to unwanted effects due to their binding of Fc-receptors. For these reasons, molecular immunologists have been concentrating on the production of the much smaller Fab- and Fv-fragments in microorganisms. These smaller fragments are not only much easier to produce, they are also less immunogenic, have no effector functions, and, because of their relatively small size, they are better able to penetrate tissues and tumors. In the case of the Fab-fragments, the constant domains adjacent to the variable domains play a major role in stabilizing the heavy and light chain dimer. Accordingly, while full-length or nearly full length engineered antibodies may comprise the subject fusion polypeptides, smaller, single domain engineered antibodies (that may be multivalent and multispecific) are preferred for use in the fusion polypeptides.

The Fv-fragment is much less stable, and a peptide linker may therefore be introduced between the heavy and light chain variable domains to increase stability. This construct is known as a single chain Fv(scFv)-fragment. A disulfide bond is sometimes introduced between the two domains for extra stability. Thus far, tetravalent scFv-based antibodies have been produced by fusion to extra polymerizing domains such as the streptavidin monomer that forms tetramers, and to amphipathic alpha helices. However, these extra domains can increase the immunogenicity of the tetravalent molecule.

Bivalent and bispecific antibodies can be constructed using only antibody variable domains. A fairly efficient and relatively simple method is to make the linker sequence between the $V_H$ and $V_L$ domains so short that they cannot fold over and bind one another. Reduction of the linker length to 3-12 residues prevents the monomeric configuration of the scFv molecule and favors intermolecular $V_H$-$V_L$ pairings with formation of a 60 kDa non-covalent scFv dimer "diabody" (Holliger et al., 1993, *Proc. Natl. Acad. Sci. USA* 90, 6444-6448). The diabody format can also be used for generation of recombinant bispecific antibodies, which are obtained by the non-covalent association of two single-chain fusion products, consisting of the $V_H$ domain from one antibody connected by a short linker to the $V_L$ domain of another antibody. Reducing the linker length still further below three residues can result in the formation of trimers ("triabody", about 90 kDa) or tetramers ("tetrabody", about 120 kDa) (Le Gall et al., 1999, *FEBS Letters* 453, 164-168). For a review of engineered antibodies, particularly single domain fragments, see Holliger and Hudson, 2005, *Nature Biotechnology*, 23:1126-1136. All of such engineered antibodies may be used in the fusion polypeptides provided herein.

Other multivalent engineered antibodies that may comprise the subject fusion polypeptides are described in Lu, et al., 2003, *J. Immunol. Meth.* 279:219-232 (di-diabodies or tetravalent bispecific antibodies); US Published Application 20050079170 (multimeric Fv molecules or "flexibodies"), and WO99/57150 and Kipriyanov, et al., 1999, J. Mol. Biol. 293:41-56 (tandem diabodies, or "Tandabs").

An engineered antibody may specifically bind, e.g., to a tumor cell antigen of a cancer to be treated or prevented by the methods of the present invention. Such antigens include, but are not limited to, for example, antigens of a human sarcoma cell or carcinoma cell, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease cell.

Engineered antibodies may specifically bind other antigens, including disease-associated and/or viral antigens. An engineered antibody may specifically bind diseased and/or virally infected cells expressing antigen on their surface.

Infectious diseases that can be treated or prevented by the methods of the present invention are caused by infectious agents. Such infectious agents or antigens derived therefrom, that may be targeted by an engineered antibody of the present invention, include, but are not limited to, viruses, bacteria, fungi, and protozoa. The invention is not limited to treating or preventing infectious diseases caused by intracellular pathogens but is intended to include extracellular pathogens as well. Many medically relevant microorganisms have been described extensively in the literature, e.g., see C. G. A Thomas, Medical Microbiology, Bailliere Tindall, Great Britain 1983, the entire contents of which is hereby incorporated by reference.

Infectious viruses of both human and non-human vertebrates, include retroviruses, RNA viruses and DNA viruses expressing antigen. Examples of viral antigens include but are not limited to antigens of: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class I=internally transmitted; class 2=parenterally transmitted (i.e. Hepatitis C); Norwalk and related viruses, and astroviruses).

Retroviral antigens that may be targeted include antigens of both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of antigens of RNA viruses that may be bound by an engineered antibody include, but are not limited to, antigens of the following: members of the family Reoviridae, including the genus *Orthoreovirus* (multiple serotypes of both mammalian and avian retroviruses), the genus *Orbivirus* (Bluetongue virus, Eugenangee virus, Kemerovo virus, African horse sickness virus, and Colorado Tick Fever virus), the genus *Rotavirus* (human rotavirus, Nebraska calf diarrhea virus, murine rotavirus, simian rotavirus, bovine or ovine rotavirus, avian rotavirus); the family Picornaviridae, including the genus *Enterovirus* (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus *Cardiovirus* (Encephalomyocarditis virus (EMC), Mengovirus), the genus *Rhinovirus* (Human rhinoviruses including at least 113 subtypes; other rhinoviruses), the genus *Apthovirus* (Foot and Mouth disease (FMDV); the family Calciviridae, including Vesicular exanthema of swine virus, San Miguel sea lion virus, Feline picornavirus and Norwalk virus; the family Togaviridae, including the genus *Alphavirus* (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza virus* (Influenza virus type A, many human subtypes); Swine influenza virus, and Avian and Equine Influenza viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza virus* (Influenza virus type A, many human subtypes); Swine influenza virus, and Avian and Equine Influenza viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); the family Rhabdoviridae, including the genus *Vesiculovirus* (VSV), ChanBipura virus, Flanders-Hart Park virus), the genus *Lyssavirus* (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viral antigens include, but are not limited to antigens of the family Poxviridae, including the genus *Orthopoxvirus* (Variola major, Variola minor, Monkey pox Vaccinia, Cowpox, Buffalopox, Rabbitpox, Ectromelia), the genus *Leporipoxvirus* (Myxoma, Fibroma), the genus *Avipoxvirus* (Fowlpox, other avian poxvirus), the genus *Capripoxvirus* (sheeppox, goatpox), the genus *Suipoxvirus* (Swinepox), the genus *Parapoxvirus* (contagious postular dermatitis virus, pseudocowpox, bovine popular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus *Mastadenovirus* (Human subgroups A, B, C, D, E and ungrouped; simian adenoviruses (at least 23 serotypes), infectious canine hepatitis, and adenoviruses of cattle, pigs, sheep, frogs and many other species, the genus *Aviadenovirus* (Avian adenoviruses); and non-cultivatable adenoviruses; the family Papoviridae, including the genus *Papillomavirus* (Human papilloma viruses, bovine papilloma viruses, Shope rabbit papilloma virus, and various pathogenic papilloma viruses of other species), the genus *Polyomavirus* (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus *Adeno*-associated viruses, the genus *Parvovirus* (Feline panleukopenia virus, bovine parvovirus, canine parvovirus, Aleutian mink disease virus, etc). Finally, DNA viral antigens may include viral antigens of viruses which do not fit into the above families such as Kuru and Creutzfeldt-Jacob disease viruses and chronic infectious neuropathic agents.

Any of the above-described multivalent engineered antibodies may be developed by one of skill in the art using routine recombinant DNA techniques, for example as described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; Beidler et al. (1988) *J. Immunol.* 141:4053-4060; and Winter and Milstein, Nature, 349, pp. 293-99 (1991)). Preferably non-human antibodies are "humanized" by linking the non-human antigen binding domain with a human constant domain (e.g. Cabilly et al., U.S. Pat. No. 4,816,567; Morrison et al., Proc. Natl. Acad. Sci. U.S.A., 81, pp. 6851-55 (1984)).

The antigen recognition sites or entire variable regions of the engineered antibodies may be derived from one or more parental antibodies directed against any antigen of interest. The parental antibodies can include naturally occurring antibodies or antibody fragments, antibodies or antibody fragments adapted from naturally occurring antibodies, antibodies constructed de novo using sequences of antibodies or antibody fragments known to be specific for an antigen of interest. Sequences that may be derived from parental antibodies include heavy and/or light chain variable regions and/or CDRs, framework regions or other portions thereof.

Multivalent, multispecific antibodies may contain a heavy chain comprising two or more variable regions and/or a light chain comprising one or more variable regions wherein at least two of the variable regions recognize different epitopes on the same antigen.

Candidate engineered antibodies for inclusion in the fusion polypeptides, or the fusion polypeptides themselves, may be screened for activity using a variety of known assays. For example, screening assays to determine binding specificity are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y., 1988, Chapter 6.

Further provided are methods of selecting candidate engineered antibodies. For example, candidates may be derived from human scFv and other antibody libraries. Accordingly, provided are antibody bacterial display libraries. A library preferably comprises a plurality of bacteria wherein the bacterial display, on average, has at least one copy of a scFv or $V_H$ or $V_L$; the library comprises a plurality of species of scFv or $V_H$ or $V_L$. In preferred embodiments, the bacterial display, on average, comprises at least 3, at least 4, or at least 5 copies of a scFv or $V_H$ or $V_L$ per bacterium. Particularly preferred libraries comprise, on average, at least about $10^6$, preferably at least about $10^7$, more preferably at least about $10^8$ different species of scFv or $V_H$ or $V_L$. In a most preferred embodiment, the antibodies are encoded by a nucleic acid that is part of plasmid or phagemid vectors. In still yet another embodiment, this invention provides a nucleic acid library encoding as the bacterial display antibody libraries. The nucleic acid library comprises at least about $10^6$, more preferably at least about $10^7$, and most preferably at least about $10^8$ different plasmid or phagemid vectors.

Endocytosed bacteria can be selected by two different methods. One way is to lyse and plate these mammalian cells on bacterial media containing appropriate antibiotic markers but such procedures are cumbersome and laborious when a large library of $>10^8$ variants has to be screened. Another approach is to express a fluorescent protein such as GFP in *E. coli*, and once endocytosed, the mammalian cell is fluorescent and can be isolated by FACS. GFP is a novel fluorescent marker to select for bacteria that are endocytosed because of the following features: a) GFP is a cytoplasmic protein with low toxicity (Chalfie et. al., *Science* 263:802, 1994); therefore, the presence of GFP should have minimal effects on the bacterial cell surface dynamics; b) GFP can be continuously synthesized, which minimizes the effect of fluorescence-signal dilution during bacterial replication; and c) GFP is easily imaged and quantitated (Wang and Hazelrigg, *Nature* 369: 400, 1994). Furthermore, the fluorescence intensity of a single mammalian cell is directly proportional to the number of bacteria associated with it (Valdivia et. al., *Gene* 173:47, 1996). Therefore, flow cytometric analysis of GFP-producing bacteria associated with host cells provides a rapid and convenient measurement of bacterial adherence and invasion. It has been shown that a) the gene gfp is expressed and a functional fluorescent GFP is produced in diverse bacterial systems such as *E. coli, Yersinia pseudotuberculosis, Salmonella typhimurium,* and *Mycobacterium marinum*, b) production of GFP did not alter the interaction of three pathogens with their respective host cells, c) intracellular bacterial pathogens producing GFP can be imaged in association with live cells and tissues, and d) GFP production can be detected by flow cytometry and be used to measure the degree of bacterial association with mammalian cells (Valdivia et. al. supra).

It is possible to directly select internalizing antibody candidates from large non-immune or immune bacterial display libraries by recovering internalized bacteria from within mammalian cells after receptor-mediated endocytosis. Thus, in one embodiment, this invention provides methods of selecting polypeptide or antibody domains that are internalized into specific target cells. The methods involve a) contacting one or more of target cells with one or more members of a bacterial display library; b) culturing the target cells under conditions where members of the display library can be internalized; and c) identifying internalized members of the bacterial display library if members of the bacterial display library are internalized into one or more of the target cells. Preferably, the methods additionally involve contacting members of the bacterial display library with cells of subtractive cell lines; and then washing the target cells to remove the cells of a subtractive cell line; and to remove members of the bacterial display library that are non-specifically bound or weakly bound to the target cells. In a preferred embodiment, the bacterial display library is an antibody bacterial display library, more preferably an antibody bacterial display library displaying single chain antibodies (scFv), or the variable domains of either light ($V_L$) or heavy ($V_H$) chains.

In a preferred embodiment, the identifying step comprises recovering internalized bacterium and repeating steps of the process again to further select for internalizing binding moieties. In one embodiment, the recovering step involves lysing the target cells to release internalized bacterium, and subculturing the bacterium to produce bacteria for a subsequent round of selection. The recovering step can involve recovering infective bacterium, and/or recovering a nucleic acid encoding a bacterial-displayed antibody and/or selection of bacteria expressing a selectable marker. The identifying step can involve detecting expression of a reporter gene, detecting the presence or quantity of a particular nucleic acid, or selection of bacterium via a selectable marker. The identifying step can also involve sorting of mammalian cells with internalized bacteria by FACS. In preferred methods, the cells of a subtractive cell line are present in at least 2-fold excess over the target cells. In preferred methods, the target cell line is grown adherent to a tissue culture plate and co-incubated with the subtracting cell line in suspension in a single culture flask. In particularly preferred methods, the contacting with a subtractive cell line is performed at a temperature (for example, at 4° C.) lower than the internalization culture conditions (for example, at 37° C.). In particularly preferred embodiments, the bacteria express a selectable marker and/or a reporter gene. Preferred selectable markers include, but are not limited to genes (or cDNAs) encoding fluorescent proteins (for example, GFP), and a chromogenic gene or cDNA (for example, beta lactamase, luciferase, and beta galactosidase). In certain embodiments, the target cells can include cells that over express a particular receptor, members of a cDNA expression library, cells that over express a chemokine receptor, cells of a transformed cell line, cells transformed with a gene or cDNA encoding a specific surface target receptor. Suitable subtractive cell lines include, but are not limited to normal human fibroblasts, normal human breast cells, pancreatic cells, and cardiomyocytes.

The cell-surface receptors involved in receptor-mediated endocytosis can be identified de novo (Gao et. al., *J. Immunol. Meth.* 274:185, 2003). In the first step, through a subtractive approach, the tumor-specific internalizing scFvs are isolated by sequentially exposing the scFv library to various human cells and then finally to the desired cell type. As the next step, the selected scFvs are used as probes for the subsequent identification of their cognate receptors by immunoprecipitation, mass spectrometry and database searching. Based on this procedures scFvs specific to transferrin receptor in prostate tumor cells, and $\alpha_3\beta_1$ integrin present in pancreatic adenocarcinoma cells were selected (Gao et. al., supra). Such a subtractive approach has been successfully used to select internalizing receptors on human breast and pancreatic carcinoma cell lines (Fransson et. al., *Cancer Lett.* 208:235, 2004) as well as on prostate carcinoma cells (Liu et. al., *Cancer Res.* 64:704, 2004).

Accordingly, the methods of this invention may also be used to identify internalizing receptors. Identifying an endocytosing receptor present only in hepatocytes (liver cells) and not in any other cell types is one such example. The methods generally involve any of the methods for identifying internalizing antibodies or polypeptides identified are used to probe the original target cells, or different cells. As the internalizing antibodies or polypeptides so bind, they permit isolation of the cell bearing the internalizing receptor and isolation of the receptor and/or the receptor epitope itself. Thus, in one embodiment the methods involve a) contacting one or more of the target cells with one or more members of a bacterial display library, b) optionally, but preferably, contacting members of the bacterial display library with cells of a subtractive cell line, c) optionally, but preferably, washing the target cells to remove said cells of a subtractive cell line and to remove members of the bacterial display library that are non-specifically bound or weakly bound or weakly bound to said target cells, d) culturing the cells under conditions where members of said bacterial display library can be internalized if bound to an internalizing marker, e) identifying internalized members of the bacterial display library if members of the bacterial display library are internalized into one or more of said target cells, f) contacting the same or different target cells with the identified internalized members of step (e) or members propagated therefrom, whereby the members bind to the surface of said target cells. The method can further involve isolating a component of the same or different target cells to which the members bind. In some methods the "identifying" step involves recovering internalized bacteria and repeating steps (a-e) to further select for internalizing receptors. The contacting, washing, culturing, and identifying steps are preferably performed as described herein, and the subtractive cell lines include cardiomyocytes, normal and cancerous breast cells.

Other protein display technologies may be used in the above-described methods. Modification of such methods to incorporate other display technologies is well known to one of skill in the art. A review of exemplary protein display technologies that may be used in the present methods is provided below.

Protein Display Technologies:

Antibody engineering plays a critical role in developing antibody therapies with superior pharmacokinetic and pharmacodynamic properties (Burks et. al., *Proc. Natl. Acad. Sci. USA* 94:412, 1997; U.S. Pat. No. 6,180,341). Directed evolution involves, first, the generation of a recombinant library of protein-expressing clones with randomized sequences using molecular biology techniques, and second, the use of screening technologies for the isolation of protein variants that exhibit the most enhanced activity. The screening of large libraries requires a physical link among a gene, the protein it encodes, and the desired function. Such a link can be established by using a variety of in vivo display technologies that have proven to be invaluable (Wittrup, *Nature Biotechnol.* 18:1039, 2000; Hayhurst and Georgiou, *Curr. Opin. Chem. Biol.* 5:683, 2001).

Protein display technologies collectively represent one of the most powerful tools for protein engineering (Olsen et. al., *Curr. Opin. Biotechnol.* 11:331, 2000). For display purposes, a protein is fused to the C or N terminus of a polypeptide sequence that targets the resulting chimera onto the surfaces of biological particles such as viruses, bacteria, and yeast. Libraries are typically screened for ligand binding by a series of adsorption-desorption cycles by a process called "panning." Panning has been used successfully to screen highly complex libraries made by cloning the mammalian antibody repertoire and displaying it on phage (up to $10^{11}$ clones). For somewhat less diverse libraries (up to $10^9$ clones), display on bacteria or yeast coupled with flow cytometry is a powerful tool for the discovery of proteins with exceptionally high ligand-binding affinities (Chen et. al., *Nature Biotechnol.* 19:537, 2001). Although the importance of display technologies for protein engineering is undisputed, the need to anchor the target polypeptide onto the surface of a biological particle imposes a number of limitations that can significantly reduce the diversity of the library relative to the totality of proteins that can be produced in a soluble form within the cell. First, protein display requires that the protein of interest be expressed as either a C- or N-terminal fusion, a process that can adversely affect protein function and/or stability. Second, protein display is subject to biological constraints associated with protein export and presentation, which may compromise the viability of the virus or cell. Third, display can introduce screening artifacts such as avidity effects in phages (O'Connell et. al., *J. Mol. Biol.* 321:49, 2002).

Candidate engineered antibodies may selected through a combination of protein display technologies, particularly bacterial display technology—involving the construction of anchored periplasmic expression (APEx) libraries in the bacterial periplasm as well as libraries expressed in bacterial cytoplasm, such that the candidate engineered antibodies are properly folded and functionally active under physiologically reducing environments of the cytosol.

One approach that has been is the isolation of scFvs from phage display libraries followed by screening large numbers of clones for expression in *E. coli* or function in mammalian cells (Lecerf et. al., *Proc. Natl. Acad. Sci. USA* 98:4764, 2001; Gennari et. al., *J. Mol. Biol.* 335:193, 2004; Emadi et. al., *Biochemistry* 43:2871, 2004). Others have used the two-hybrid system to isolate engineered antibodies (Tes et. al., *J. Mol. Biol.* 317:85, 2002; Tanaka et. al., *EMBO J.* 22:1025, 2003), but this does not allow for fine-tuning of the antibody biophysical properties such as affinity and expression.

A: Phage Display Library:

Display on M13 bacteriophage is the oldest and the most widely used protein library-screening method (Marks et. al., *J. Mol. Biol.* 222:581, 1991; Marks et. al., *J. Biol. Chem.* 267:16007, 1992; Rodi and Makowski, *Curr. Opin. Biotechnol.* 10:87, 1999). Phage antibody libraries have become an important resource for the development of therapeutic antibodies (Bradbury and Marks, *J. Immunol. Meth.* 290:29, 2004). Large non-immune libraries serve as a single pot resource for the rapid generation of human MAbs (HuMAbs) to a wide range of self and non-self antigens, including tumor growth factor receptors (Li et. al., *Cancer Gene Ther.* 8:555, 2001; Liu et. al., *Cancer Res.* 64:704, 2004). Most of the MAbs isolated from combinatorial libraries expressed on phage have been selected using purified antigens or peptides immobilized on artificial surfaces. This approach may select MAbs that do not recognize the native protein in a physiological context, especially with large molecular mass cell surface receptors. Attempts have been made to select antigen in native conformation using either cell lysates (Parren et. al., *J. Virol.* 70:9046, 1996; Sanna et. al., *Proc. Natl. Acad. Sci. USA* 92:6439, 1995; Sawyer et. al., *J. Immunol. Meth.* 204:193, 1997) or living cells (Andersen et. al., *Proc. Natl. Acad. Sci. USA* 93:1820, 1996; Osbourn et. al., *Immunotechnol.* 3:293, 1998). Because of the heterogeneity of the starting material, such approaches require elaborate protocols including subtractive steps to avoid the selection of irrelevant antibodies. The few successful selections performed on heterogenous material were generally done using small libraries from immunized sources. The use of immunized libraries limits the spectrum of antigen specificities that can potentially be obtained from the same library and typically yield murine antibodies. There are only three reports of successful selection on cells using large non-immune libraries (de Kruif et. al., *Proc. Natl. Acad. Sci. USA* 92:3938, 1995; Marks et. al., *Biotechnology* 11:1145, 1993; Vaughan et. al., *Nature Biotechnol.* 14:309, 1996).

The step limiting the selection of binders from large naïve libraries by cell panning seems to be the relatively high background binding of non-specific phage and relatively low binding of specific phage (Becerril et. al., *Biochem. Biophys. Res. Comm.* 255:386, 1999; Pereira et. al., *J. Immunol. Meth.* 203:11, 1997; Watters et. al., *Immunotechnol.* 3:21, 1997). The low binding of specific phage is partially related to the low concentration of a given binding phage in the polyclonal preparation (approximately $1.6 \times 10^{-17}$ M for a single member of a $10^9$ library in a phage preparation of $1 \times 10^{13}$ particles/ml). The low concentration simultaneously limits the efficiency of both subtraction of common binders and enrichment of specific binders. To overcome this limitation, it was resorted to take advantage of normal cell surface receptor biology. Many receptors undergo endocytosis upon ligand binding. It was hypothesized that enrichment ratios of specific binders could be significantly increased by recovering endocytosed phage antibodies from the cytosol after stringent removal of non-specific phage from the cell surface (Poul et. al., *J. Mol. Biol.* 301:1149, 2000).

B: Yeast Surface Display Library:

Yeast surface display (YSD; Boder and Wittrup, *Nature Biotechnol.* 15:553, 1997) is another proven tool for protein engineering. In YSD, the protein of interest is expressed as a fusion with a yeast mating protein, Aga2p, which is targeted to the yeast cell wall. Once expressed on the yeast surface, protein properties such as stability and affinity, can be quantitatively measured using fluorescently labeled reagents and flow cytometry. Further, libraries of mutants can be sorted for desired properties using fluorescent activated cell sorting (FACS). YSD has been successfully applied to several facets of antibody engineering: isolation of novel Abs against specific antigens from a non-immune HuMAb library (Feldhaus et. al., *Nature Biotechnol.* 21:163, 2003); affinity maturation resulting in the highest affinity antibody reported to date (Boder et. al., *Proc. Natl. Acad. Sci. USA* 97:10701, 2000); and stability and extracellular expression optimization (Shusta et. al., *Nature Biotechnol.* 18:754, 2000). In addition, YSD is a useful tool for domain-level analysis of an antibody's binding site (paratope), and engineering of functional antibodies (Colby et. al., *J. Mol. Biol.* 342:901, 2004). In an attempt to identify a minimal antibody fragment with superior expression and intracellular function, YSD was used to engineer an intracellularly non-functional scFv into a functional single-domain $V_L$ antibody through affinity maturation and binding site analysis.

Not withstanding all these advantages, a potential shortcoming of the YSD platform for application to antibody engineering might arise from the difference in redox environment on the cell surface as compared to the cytoplasm, where disulfide bonds do not stably form. MAbs contain highly conserved intradomain disulfide bonds in both the $V_H$ and $V_L$ domains that hold the β-sheet-forming framework residues in a rigid conformation. Disruption of these disulfide bonds perturbs the domain structure, reducing protein stability (Ramm et. al., *J. Mol. Biol.* 290:535, 1999). This presumably is responsible for the disparity between cell surface expression and cytoplasmic expression levels for the scFv. Further, the expression of fusion proteins (for example, scFv) is generally cis-dominant; that is, the expression of the fusion protein is only as good as the expression of the member with the lowest stability, so an alternative explanation of the improvement in expression observed when the $V_H$ is eliminated is that the $V_H$ domain of 2.4.3 was significantly less stable than the $V_L$ under reducing conditions (Colby et. al., supra).

An important issue with any library screening technology (both phage and yeast display technologies) is the ability to express isolated clones at a high level. Existing display formats involve fusion to large anchoring sequences, which can influence the expression characteristics of the displayed proteins. For this reason, scFvs that display well as fusions in phage, yeast, or bacteria (particularly the protein libraries expressed on the outer membrane) may not necessarily be amenable to high expression in soluble form as nonfusion proteins (Hayhurst et. al., *J. Immunol. Meth.* 276:185, 2003). In contrast, the short (6-aa) sequence required for N-terminal tethering of proteins onto the cytoplasmic membrane in APEx display is unlikely to affect the expression characteristics of the fusion. Consistent with this hypothesis, all three affinity-enhanced clones to the anthrax PA toxin isolated by APEx exhibited excellent soluble expression characteristics despite having numerous amino acid substitutions, suggesting that the isolation of clones that can readily be produced in soluble form in bacteria on a large scale may be an intrinsic feature of APEx selections (Harvey et. al., *Proc. Natl. Acad. Sci. USA* 101:9193, 2004).

C: APEx Bacterial Display Library:

A flow cytometry-based method has been developed using bacterial expression for the efficient selection of high-affinity ligand-binding proteins, and specifically scFvs, from combinatorial libraries. APEx is based on the anchoring of proteins to the periplasmic side of the inner membrane, followed by disruption of the outer membrane before incubation with fluorescently labeled antigen and FC sorting (Harvey et. al., *Proc. Natl. Acad. Sci. USA* 101:9193, 2004). In APEx, proteins are expressed in periplasm by tethering to the inner membrane of *E. coli*. After chemical/enzymatic permeabilization of the bacterial outer membrane, *E. coli* cells expressing anchored scFv antibodies can be specifically labeled with fluorescent antigens, ranging in size up to at least 240 kDa, and analyzed by FC. Another advantage is that fusions between GFP and antigen can be expressed endogenously and captured by periplasmically anchored scFv. Thus, after a washing step, cells that express both the fluorescent antigen and an APEx-anchored scFv are highly fluorescent and can be readily sorted from cells that express either only an scFv or GFP-antigen fusion alone.

With sorting rates of >400 million cells per hour, commercial FC machines can be used to screen libraries of the size accessible within the constraints of microbial transformation efficiencies. Furthermore, multiparameter FC can provide valuable information regarding the function of each and every library clone in real time, thus helping to guide the library construction process and optimize sorting conditions (Daugherty, P. S. et. al., *Proc. Natl. Acad. Sci. USA* 97:2029, 2000). In particular, *E. coli* offers facile expression of recombinant protein and high DNA transformation efficiencies that allow for efficient large library production and increased coverage of protein library sequence space.

APEx display offers several advantages over previously developed bacterial periplasmic expression with cytometric screening method, called PECS (Chen et. al., *Nature Biotechnol.* 19:537, 2001), as well as surface display approaches such as phage and yeast display technologies: (i) APEX is an *E. coli* based system and therefore provides an easy route to the creation of large libraries by transformation and preparative protein expression of isolated antibodies; (ii) by using a fatty acylated anchor to retain the protein in the inner membrane, a fusion as short as 6 amino acids is all that is required for display. The short fusion is unlikely to influence the affinity or expression characteristics of the isolated proteins; (iii) the inner membrane lacks molecules such as LPS or other complex carbohydrates that can sterically interfere with large antigen binding to displayed polypeptides; (iv) the fusion must only traverse one membrane before it is displayed, and therefore biosynthetic limitations that might restrict the export of certain sequences to the yeast or bacterial surface may be circumvented; (v) display is accomplished by using either N- or C-terminal fusion, (vi) APEx can be used directly for proteins expressed from widely used phage display vectors. Finally, (vii) APEx provides a means for the simultaneous expression of fluorescent antigen and antibodies within the same cell. This is particularly important for peptide antigens, and circumvents time-consuming processes for synthesis, purification, and conjugation of preparative amounts of probe, as is required when the fluorescent antigen is incubated with the library. APEx can be used for the detection of antigens ranging from small molecules (<1 kDa) to phycoerythrin conjugates (240 kDa), and possibly much larger antigens.

APEx display procedure can be used to derive a single domain antibodies (DAbs) from an scFv, when the binding energy of the scFv is contributed predominantly by one of the two domains.

B. HSP70 Domains

Any suitable stress protein (heat shock protein (Hsp)) can be used in the fusion polypeptides of the present invention. For example, Hsp60 and/or Hsp70 can be used. Turning to stress proteins generally, cells respond to a stressor (typically heat shock treatment) by increasing the expression of a group of genes commonly referred to as stress, or heat shock, genes. Heat shock treatment involves exposure of cells or organisms to temperatures that are one to several degrees Celsius above the temperature to which the cells are adapted. In coordination with the induction of such genes, the levels of corresponding stress proteins increase in stressed cells.

In bacteria, the predominant stress proteins are proteins with molecular sizes of about 70 and 60 kDa respectively, that are commonly referred to as Hsp70 and Hsp60. respectively. These and other specific stress proteins and the genes encoding them are discussed further below. In bacteria, Hsp70 and Hsp60 typically represent about 1-3% of cell protein based on the staining pattern using sodium dodecyl sulfate polyacrylamide gel electrophoresis and the stain Coomassie blue, but accumulate to levels as high as 25% under stressful conditions. Stress proteins appear to participate in important cellular processes such as protein synthesis, intracellular trafficking, and assembly and disassembly of protein complexes. It appears that the increased amounts of stress proteins synthesized during stress serve primarily to minimize the consequences of induced protein unfolding. Indeed, the preexposure of cells to mildly stressful conditions that induce the synthesis of stress proteins affords protection to the cells from the deleterious effects of a subsequent more extreme stress.

The major stress proteins appear to be expressed in every organism and tissue type) examined so far. Also, it appears that stress proteins represent the most highly conserved group of proteins identified to date. For example, when stress proteins in widely diverse organisms are compared, Hsp90 and Hsp70 exhibit 50% or higher identity at the amino acid level and share many similarities at non-identical positions. It is noted that similar or higher levels of homology exist between different members of a particular stress protein family within species.

The stress proteins, particularly Hsp70, Hsp60, Hsp20-30 and Hsp 10, are among the major determinants recognized by the host immune system in the immune response to infection by *Mycobacterium tuberculosis* and *Mycobacterium leprae*. Young, R. A. and Elliott. T. J., Stress Proteins, Infection, And Immune Surveillance, *Cell* 50:5-8 (1989). Further, some rat arthritogenic T cells recognize Hsp60 epitopes. Van Eden, W. et al., Nature 331:171-173 (1988). However, individuals, including healthy individuals, with no history of mycobacterial infection or autoimmune disease also carry T cells that recognize both bacterial and human Hsp60 epitopes; a considerable fraction of T cells in healthy individuals that are characterized by expression of the gamma-delta T cell receptor recognize both self and foreign stress proteins. O'Brien, R. et al., *Cell* 57:664-674 (1989). Thus, individuals, even healthy individuals possess T-cell populations that recognize both foreign and self stress protein epitopes.

This system recognizing stress protein epitopes presumably constitutes an "early defense system" against invading organisms. Murray, P. J. and Young, R. A., *J. Bacteriol* 174: 4193-6 (1992). The system may be maintained by frequent stimulation by bacteria and viruses. As discussed before, healthy individuals have T cell populations recognizing self stress proteins. Thus, the presence of autoreactive T cells is compatible with normal health and does not cause autoimmune disease; this demonstrates the safety of stress proteins within an individual. The safety of stress proteins is additionally demonstrated by the success and relative safety of BCG (Bacille Calmette Guerin, a strain of *Mycobacterium bovis*) vaccinations, which induce an immune response against stress proteins that is also protective against *Mycobacterium tuberculosis*.

Families of stress genes and proteins for use in the fusion polypeptides are those well known in the art and include, for example, Hsp 100-200, Hsp100, Hsp90, Lon, Hsp70, Hsp60, TF55, Hsp40, FKBPs, cyclophilins, Hsp20-30, ClpP, GrpE, Hsp10, ubiquitin, calnexin, and protein disulfide isomerases. Macario, A. J. L., Cold Spring Harbor Laboratory Res. 25:59-70, 1995; Parsell, D. A. & Lindquist, S. *Ann. Rev. Genet.* 27:437-496 (1993); U.S. Pat. No. 5,232,833 (Sanders et al.). A particular group of stress proteins includes Hsp90. Hsp70. Hsp60, Hsp20-30, further preferably Hsp70 and Hsp60.

Hsp100-200 examples include Grp170 (for glucose-regulated protein). Grp 170 resides in the lumen of the ER, in the pre-Golgi compartment, and may play a role in immunoglobulin folding and assembly.

Hsp100 examples include mammalian Hsp110, yeast Hsp104, ClpA, ClpB, ClpC, ClpX and ClpY. Yeast Hsp104 and *E. coli* ClpA, form hexameric and *E. coli* ClpB, tetrameric particles whose assembly appears to require adenine nucleotide binding. Clp protease provides a 750 kDa heterooligomer composed of ClpP (a proteolytic subunit) and of ClpA. ClpB-Y are structurally related to ClpA, although unlike ClpA they do not appear to complex with ClpP.

Hsp90 examples include HtpG in *E. coli*. Hsp83 and Hsc83 yeast, and Hsp90alpha. Hsp90beta and Grp94 in humans. Hsp90 binds groups of proteins, which proteins are typically cellular regulatory molecules such as steroid hormone receptors (e.g., glucocorticoid, estrogen, progesterone, and testosterone receptors), transcription factors and protein kinases that play a role in signal transduction mechanisms. Hsp90 proteins also participate in the formation of large, abundant protein complexes that include other stress proteins.

Lon is a tetrameric protein functioning as an ATP-dependent protease degrading non-native proteins in *E. coli*.

Hsp70 examples include Hsp72 and Hsc73 from mammalian cells, DnaK from bacteria, particularly mycobacteria such as *Mycobacterium leprae, Mycobacterium tuberculosis*, and *Mycobacterium bovis* (such as Bacille-Calmette Guerin: referred to herein as Hsp71), DnaK from *Escherichia coli*, yeast, and other prokaryotes, and BiP and Grp78. Hsp70 is capable of specifically binding ATP as well as unfolded polypeptides and peptides, thereby participating in protein folding and unfolding as well as in the assembly and disassembly of protein complexes.

Hsp60 examples include Hsp65 from mycobacteria. Bacterial Hsp60 is also commonly known as GroEL, such as the GroEL from *E. coli*. Hsp60 forms large homooligomeric complexes, and appears to play a key role in protein folding. Hsp60 homologues are present in eukaryotic mitochondria and chloroplasts.

TF55 examples include Tcpl, TRiC and thermosome. The proteins typically occur in the cytoplasm of eukaryotes and some archaebacteria, and form multi-membered rings, promoting protein folding. They are also weakly homologous to Hsp60.

Hsp40 examples include DnaJ from prokaryotes such as *E. coli* and mycobacteria and HSJ1, HDJ1 and Hsp40. Hsp40 plays a role as a molecular chaperone in protein folding, thermotolerance and DNA replication, among other cellular activities.

FKBPs examples include FKBP12, FKBP13, FKBP25, and FKBP59, Fprl and Nepl. The proteins typically have peptidyl-prolyl isomerase activity and interact with immunosuppressants such as FK506 and rapamycin. The proteins are typically found in the cytoplasm and the endoplasmic reticulum.

Cyclophilin examples include cyclophilins A, B and C. The proteins have peptidyl-prolyl isomerase activity and interact with the immunosuppressant cyclosporin A. The protein cyclosporin A binds calcineurin (a protein phosphatase).

Hsp20-30 is also referred to as small Hsp. Hsp20-30 is typically found in large homooligomeric complexes or, possibly, also heterooligomeric complexes where an organism or cell type expresses several different types of small Hsps. Hsp20-30 interacts with cytoskeletal structures, and may play a regulatory role in the polymerization/depolymerization of actin. Hsp20-30 is rapidly phosphorylated upon stress or exposure of resting cells to growth factors. Hsp20-30 homologues include alpha-crystallin.

ClpP is an *E. coli* protease involved in degradation of abnormal proteins. Homologues of ClpP are found in chloroplasts. ClpP forms a heterooligomeric complex with ClpA.

GrpE is an *E. coli* protein of about 20 kDa that is involved in both the rescue of stress-damaged proteins as well as the degradation of damaged proteins. GrpE plays a role in the regulation of stress gene expression in *E. coli*.

Hsp10 examples include GroES and Cpn10. Hsp10 is typically found in *E. coli* and in mitochondria and chloroplasts of eukaryotic cells. Hsp10 forms a seven-membered ring that associates with Hsp60 oligomers. Hsp10 is also involved in protein folding.

Ubiquitin has been found to bind proteins in coordination with the proteolytic removal of the proteins by ATP-dependent cytosolic proteases.

In particular embodiments, the stress proteins of the present invention are obtained from enterobacteria, mycobacteria (particularly *M. leprae, M. tuberculosis, M. vaccae, M smegmatis* and *M. bovis*), *E. coli*, yeast, *Drosophila*, vertebrates, avians, chickens, mammals, rats, mice, primates, or humans.

In particular embodiments, e.g., in cases involving chemical conjugates between a stress protein and an engineered antibody, the stress proteins used are isolated stress proteins, which means that the stress proteins have been selected and separated from the host cell in which they were produced. Such isolation can be carried out as described herein and using routine methods of protein isolation known in the art.

The stress proteins may be in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance the increased biological activity of the stress protein. Due to code degeneracy, for example, there may be considerable variation in nucleotide sequences encoding the same amino acid sequence. Portions of stress proteins or peptides obtained from stress proteins may be used in the fusion polypeptides, provided such portions or peptides include the epitopes involved with enhancing the immune response. Portions of stress proteins may be obtained by fragmentation using proteinases, or by recombinant methods, such as the expression of only part of a stress protein-encoding nucleotide sequence (either alone or fused with another protein-encoding nucleic acid sequence). Peptides may also be produced by such methods, or by chemical synthesis. The stress proteins may include mutations introduced at particular loci by a variety of known techniques, e.g., to enhance the effect on the immune system. See, e.g., Sambrook et al., Molecular Cloning: A Laboratory Manual. 2d Ed., Cold Spring Harbor Laboratory Press (1989); Drinkwater and Klinedinst *Proc. Natl. Acad. Sci. USA* 83:3402-3406 (1986); Liao and Wise, *Gene* 88:107-111 (1990): Horwitz et al., *Genome* 3:112-117 (1989).

A fusion polypeptide may comprise an amino acid sequence that is at least about 80%, 85%, 90%, 95%, 98%, or 99% identical to a stress protein described herein.

2. Methods of Making the Engineered Antibody-Stress Protein Fusion Polypeptides

Provided also are compositions and methods for making the engineered antibody-stress protein fusion polypeptides. A fusion protein including an engineered antibody and a stress protein can be produced by recombinant means. For example, a nucleic acid encoding the stress protein can be joined to either end of a nucleic acid sequence encoding the engineered antibody such that the two protein-coding sequences are sharing a common translational reading frame and can be expressed as a fusion protein including the engineered antibody and the stress protein. The combined sequence is inserted into a suitable vector chosen based on the expression features desired and the nature of the host cell. In the examples provided hereinafter, the nucleic acid sequences are assembled in a vector suitable for protein expression in the bacterium *E. coli*. Following expression in the chosen host cell, fusion protein can be purified by routine biochemical separation techniques or by immunoaffinity methods using an antibody to one or the other part of the fusion protein. Alternatively, the selected vector can add a tag to the fusion protein sequence, e.g., an oligohistidine tag as described in the examples presented hereinafter, permitting expression of a tagged fusion protein that can be purified by affinity methods using an antibody or other material having an appropriately high affinity for the tag. Sambrook et al., Molecular Cloning: A Laboratory Manual, 2d Ed., Cold Spring Harbor Laboratory Press (1989); Deutscher, M. Guide to Protein Purification Methods Enzymology, vol. 182. Academic Press, Inc. San Diego, Calif. (1990). If a vector suitable for expression in mammalian cells is used. e.g., one of the vectors discussed below, the fusion protein can be expressed and purified from mammalian cells. Alternatively, the mammalian expression vector (including fusion protein-coding sequences) can be administered to a subject to direct expression of engineered antibody-stress protein fusion polypeptide in the subject's cells. A nucleic acid encoding an engineered antibody-stress protein fusion polypeptide can also be produced chemically and then inserted into a suitable vector for fusion protein production and purification or administration to a subject. Finally, a fusion protein can also be prepared chemically.

An isolated nucleic acid composition encoding the fusion polypeptide may comprise a nucleotide sequence that is at least about 80%, 85%, 90%, 95%, 98%, or 99% identical to a nucleotide sequence encoding a stress protein described herein.

Techniques for making fusion genes are well known in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, *Current Protocols in Molecular Biology*, eds. Ausubel et al., John Wiley & Sons: 1992). Accordingly, provided is an isolated nucleic acid comprising a fusion gene of a gene encoding at least one engineered antibody and a gene encoding at least one stress protein.

The nucleic acid may be provided in a vector comprising a nucleotide sequence encoding an engineered antibody-stress protein fusion polypeptide, and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered. Such vectors may be administered in any biologically effective carrier, e.g., any formulation or composition capable of effectively transfecting cells either ex vivo or in vivo with genetic material encoding a chimeric polypeptide. Approaches include insertion of the nucleic acid in viral vectors including recombinant retroviruses, adenoviruses, adeno-associated viruses, human immunodeficiency viruses, and herpes simplex viruses-1, or recombinant bacterial or eukaryotic plasmids. Viral vectors may be used to transfect cells directly; plasmid DNA may be delivered alone with the help of, for example, cationic liposomes (lipofectin) or derivatized (e.g., antibody conjugated), polylysine conjugates, gramicidin S, artificial viral envelopes or other such intracellular carriers. Nucleic acids may also be directly injected. Alternatively, calcium phosphate precipitation may be carried out to facilitate entry of a nucleic acid into a cell.

The subject nucleic acids may be used to cause expression and over-expression of an engineered antibody-stress protein fusion polypeptide in cells propagated in culture, e.g. to produce fusion proteins or polypeptides.

Provided also is a host cell transfected with a recombinant gene in order to express an engineered antibody-stress protein fusion polypeptide. The host cell may be any prokaryotic or eukaryotic cell. For example, an engineered antibody-stress protein fusion polypeptide may be expressed in bacterial cells, such as *E. coli*, insect cells (baculovirus), yeast, insect, plant, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Other methods suitable for maximizing expression of the fusion polypeptide will be known to those in the art.

A cell culture includes host cells, media and other byproducts. Suitable media for cell culture are well known in the art. A fusion polypeptide may be secreted and isolated from a mixture of cells and medium comprising the polypeptide. Alternatively, a fusion polypeptide may be retained cytoplasmically and the cells harvested, lysed and the protein isolated. A fusion polypeptide may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of a fusion.

Thus, a nucleotide sequence encoding all or part of an engineered antibody-stress protein fusion polypeptide may be used to produce a recombinant form of a protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant fusion polypeptides by microbial means or tissue-culture technology in accord with the subject invention.

An isolated nucleic acid composition encoding the fusion polypeptide may %, 85%, 90%, 95%, 98%, or 99% identical to a nucleotide sequence encoding an engineered antibody described herein.

Expression vehicles for production of a recombinant protein include plasmids and other vectors. For instance, suitable vectors for the expression of a fusion polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

In another embodiment, the nucleic acid is an engineered antibody-stress protein fusion polypeptide operably linked to a bacterial promoter, e.g., the anaerobic *E. coli*, NirB promoter or the *E. coli* lipoprotein llp promoter, described, e.g., in Inouye et al. (1985) *Nucl. Acids Res.* 13:3101; *Salmonella* pagC promoter (Miller et al., supra), *Shigella* ent promoter (Schmitt and Payne, *J. Bacteriol.* 173:816 (1991)), the tet promoter on Tn10 (Miller et al., supra), or the ctx promoter of *Vibrio cholera*. Any other promoter can be used. The bacterial promoter can be a constitutive promoter or an inducible promoter. An exemplary inducible promoter is a promoter which is inducible by iron or in iron-limiting conditions. In fact, some bacteria, e.g., intracellular organisms, are believed to encounter iron-limiting conditions in the host cytoplasm. Examples of iron-regulated promoters of FepA and TonB are known in the art and are described, e.g., in the following references: Headley, V. et al. (1997) *Infection & Immunity* 65:818; Ochsner, U. A. et al. (1995) *Journal of Bacteriology* 177:7194; Hunt, M. D. et al. (1994) *Journal of Bacteriology* 176:3944; Svinarich, D. M. and S. Palchaudhuri. (1992) *Journal of Diarrhoeal Diseases Research* 10:139; Prince, R. W. et al. (1991) *Molecular Microbiology* 5:2823; Goldberg, M. B. et al. (1990) *Journal of Bacteriology* 172:6863; de Lorenzo, V. et al. (1987) *Journal of Bacteriology* 169:2624; and Hantke, K. (1981) *Molecular & General Genetics* 182:288.

A plasmid preferably comprises sequences required for appropriate transcription of the nucleic acid in bacteria, e.g., a transcription termination signal. The vector can further comprise sequences encoding factors allowing for the selection of bacteria comprising the nucleic acid of interest, e.g., gene encoding a protein providing resistance to an antibiotic, sequences required for the amplification of the nucleic acid, e.g., a bacterial origin of replication.

In another embodiment, a signal peptide sequence is added to the construct, such that the fusion polypeptide is secreted from cells. Such signal peptides are well known in the art.

In one embodiment, the powerful phage T5 promoter, that is recognized by *E. coli* RNA polymerase is used together with a lac operator repression module to provide tightly regulated, high level expression or recombinant proteins in *E. coli*. In this system, protein expression is blocked in the presence of high levels of lac repressor.

In one embodiment, the DNA is operably linked to a first promoter and the bacterium further comprises a second DNA encoding a first polymerase which is capable of mediating transcription from the first promoter, wherein the DNA encoding the first polymerase is operably linked to a second promoter. In a preferred embodiment, the second promoter is a bacterial promoter, such as those delineated above. In an even more preferred embodiment, the polymerase is a bacteriophage polymerase, e.g., SP6, T3, or T7 polymerase and the first promoter is a bacteriophage promoter, e.g., an SP6, T3, or T7 promoter, respectively. Plasmids comprising bacteriophage promoters and plasmids encoding bacteriophage polymerases can be obtained commercially, e.g., from Promega Corp. (Madison, Wis.) and InVitrogen (San Diego, Calif.), or can be obtained directly from the bacteriophage using standard recombinant DNA techniques (J. Sambrook, E. Fritsch, T. Maniatis, Molecular Cloning: A Laboratory Manual, Cold Spring Laboratory Press, 1989). Bacteriophage polymerases and promoters are further described, e.g., in the following references: Sagawa, H. et al. (1996) Gene 168:37; Cheng, X. et al. (1994) *PNAS USA* 91:4034; Dubendorff, J. W. and F. W. Studier (1991) *Journal of Molecular Biology* 219:45; Bujarski, J. J. and P. Kaesberg (1987) *Nucleic Acids Research* 15:1337; and Studier, F. W. et al. (1990) *Methods in Enzymology* 185:60). Such plasmids can further be modified according to the specific embodiment of the engineered antibody-stress protein fusion polypeptide to be expressed.

In another embodiment, the bacterium further comprises a DNA encoding a second polymerase which is capable of mediating transcription from the second promoter, wherein the DNA encoding the second polymerase is operably linked to a third promoter. The third promoter may be a bacterial promoter. However, more than two different polymerases and promoters could be introduced in a bacterium to obtain high levels of transcription. The use of one or more polymerases for mediating transcription in the bacterium can provide a significant increase in the amount of polypeptide in the bacterium relative to a bacterium in which the DNA is directly under the control of a bacterial promoter. The selection of the system to adopt will vary depending on the specific use, e.g., on the amount of protein that one desires to produce.

Generally, a nucleic acid encoding a fusion polypeptide is introduced into a host cell, such as by transfection, and the host cell is cultured under conditions allowing expression of the fusion polypeptide. Methods of introducing nucleic acids into prokaryotic and eukaryotic cells are well known in the art. Suitable media for mammalian and prokaryotic host cell culture are well known in the art. Generally, the nucleic acid encoding the subject fusion polypeptide is under the control of an inducible promoter, which is induced once the host cells comprising the nucleic acid have divided a certain number of times. For example, where a nucleic acid is under the control of a beta-galactose operator and repressor, isopropyl beta-D-thiogalactopyranoside (IPTG) is added to the culture when the bacterial host cells have attained a density of about $OD_{600}$ 0.45-0.60. The culture is then grown for some more time to give the host cell the time to synthesize the polypeptide. Cultures are then typically frozen and may be stored frozen for some time, prior to isolation and purification of the polypeptide.

When using a prokaryotic host cell, the host cell may include a plasmid which expresses an internal T7 lysozyme, e.g., expressed from plasmid pLysSL (see Examples). Lysis of such host cells liberates the lysozyme which then degrades the bacterial membrane.

Other sequences that may be included in a vector for expression in bacterial or other prokaryotic cells include a synthetic ribosomal binding site; strong transcriptional terminators, e.g., $t_o$ from phage lambda and $t_4$ from the rrnB operon in *E. coli*, to prevent read through transcription and ensure stability of the expressed polypeptide; an origin of replication, e.g., ColE1; and beta-lactamase gene, conferring ampicillin resistance.

Other host cells include prokaryotic host cells. Even more preferred host cells are bacteria, e.g., *E. coli*. Other bacteria that can be used include *Shigella* spp., *Salmonella* spp., *Listeria* spp., *Rickettsia* spp., *Yersinia* spp., *Escherichia* spp., *Klebsiella* spp., *Bordetella* spp., *Neisseria* spp., *Aeromonas* spp., *Francisella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., and *Erysipelothrix* spp. Most of these bacteria can be obtained from the American Type Culture Collection (ATCC; 10801 University Blvd., Manassas, Va. 20110-2209).

A number of vectors exist for the expression of recombinant proteins in yeast. For instance, YEP24, YIPS, YEP51, YEP52, pYES2, and YRP17 are cloning and expression vehicles useful in the introduction of genetic constructs into *S. cerevisiae* (see, for example, Broach et al., (1983) in *Experimental Manipulation of Gene Expression*, ed. M. Inouye Academic Press, p. 83). These vectors may replicate in *E. coli* due the presence of the pBR322 ori, and in *S. cerevisiae* due to the replication determinant of the yeast 2 micron plasmid. In addition, drug resistance markers such as ampicillin may be used.

In certain embodiments, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the B-gal comprising pBlueBac III).

In another variation, protein production may be achieved using in vitro translation systems. In vitro translation systems are, generally, a translation system which is a cell-free extract comprising at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. An RNA nucleotide for in vitro translation may be produced using methods known in the art. In vitro transcription and translation may be coupled in a one-pot reaction to produce proteins from one or more isolated DNAs.

When expression of a carboxy terminal fragment of a polypeptide is desired, i.e. a truncation mutant, it may be necessary to add a start codon (ATG) to the oligonucleotide fragment comprising the desired sequence to be expressed. It is well known in the art that a methionine at the N-terminal position may be enzymatically cleaved by the use of the enzyme methionine aminopeptidase (MAP). MAP has been cloned from *E. coli* (Ben-Bassat et al., (1987) *J. Bacteria* 169:751-757) and *Salmonella typhimurium* and its in vitro activity has been demonstrated on recombinant proteins (Miller et al., (1987) *PNAS USA* 84:2718-1722). Therefore, removal of an N-terminal methionine, if desired, may be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

In cases where plant expression vectors are used, the expression an engineered antibody-stress protein fusion polypeptide may be driven by any of a number of promoters. For example, viral promoters such as the 35S RNA and 19S RNA promoters of CaMV (Brisson et al., 1984, Nature, 310: 511-514), or the coat protein promoter of TMV (Takamatsu et al., 1987, EMBO J., 6:307-311) may be used; alternatively, plant promoters such as the small subunit of RUBISCO (Coruzzi et al., 1994, EMBO J., 3:1671-1680; Broglie et al., 1984, Science, 224:838-843); or heat shock promoters, e.g., soybean Hsp 17.5-E or Hsp 17.3-B (Gurley et al., 1986, Mol. Cell. Biol., 6:559-565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, New York, Section VIII, pp. 421-463; and Grierson & Corey, 1988, Plant Molecular Biology, 2d Ed., Blackie, London, Ch. 7-9.

An alternative expression system which can be used to express a polypeptide tag or fusion protein comprising a polypeptide tag is an insect system. In one such system, *Autographa californica* nuclear polyhedrosis virus (AcNPV) is used as a vector to express foreign genes. The virus grows in *Spodoptera frugiperda* cells. The PGHS-2 sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Virol., 46:584, Smith, U.S. Pat. No. 4,215,051).

In a specific embodiment of an insect system, the DNA encoding an engineered antibody-stress protein fusion polypeptide is cloned into the pBlueBacIII recombinant transfer vector (Invitrogen, San Diego, Calif.) downstream of the polyhedron promoter and transfected into Sf9 insect cells (derived from *Spodoptera frugiperda* ovarian cells, available from Invitrogen, San Diego, Calif.) to generate recombinant virus. After plaque purification of the recombinant virus high-titer viral stocks are prepared that in turn would be used to infect Sf9 or High Five™ (BTI-TN-5BI-4 cells derived from *Trichoplusia ni* egg cell homogenates; available from Invitrogen, San Diego, Calif.) insect cells, to produce large quantities of appropriately post-translationally modified subject polypeptide.

In other embodiments, an engineered antibody and stress protein are produced separately and then linked, e.g. covalently linked, to each other. For example, an engineered antibody and stress protein are produced separately in vitro, purified, and mixed together under conditions under which the tag will be able to be linked to the polypeptide of interest. For example, the stress protein and/or the engineered antibody can be obtained (isolated) from a source in which it is known to occur, can be produced and harvested from cell cultures, can be produced by cloning and expressing a gene encoding the desired stress protein or engineered antibody, or can be synthesized chemically. Furthermore, a nucleic acid sequence encoding the desired stress protein or engineered antibody can be synthesized chemically. Such mixtures of conjugated proteins may have properties different from single fusion proteins.

The present invention consists of both a non-chemical and chemical method to link an engineered antibody to *Mycobacterium tuberculosis* HSP70 protein for the purpose of vaccination against the target antigen(s) and/or cells expressing said target antigen(s). A fusion construct consisting of an antibody binding element and *Mycobacterium tuberculosis* HSP70 may be generated. The antibody binding element may consist for example of: Protein A, Protein G or Protein L or any protein segment(s) demonstrating high binding affinity for antibodies and/or scFvs. When needed, appropriate engineered antibodies such as scFV's could be generated quickly, and stoichiometrically mixed with preformed PL-MTb HSP 70 fusion, creating the newly targeted scFv-PL-MTb HSP 70 fusion vaccine.

Linkers (also known as "linker molecules" or "cross-linkers") may be used to conjugate an engineered antibody and stress protein. Linkers include chemicals able to react with a defined chemical group of several, usually two, molecules and thus conjugate them. The majority of known cross-linkers react with amine, carboxyl, and sulfhydryl groups. The choice of target chemical group is crucial if the group may be involved in the biological activity of the polypeptides to be conjugated. For example, maleimides, which react with sulfhydryl groups, may inactivate Cys-comprising peptides or proteins that require the Cys to bind to a target. Linkers may be homofunctional (comprising reactive groups of the same type), heterofunctional (comprising different reactive groups), or photoreactive (comprising groups that become reactive on illumination).

Linker molecules may be responsible for different properties of the conjugated compositions. The length of the linker should be considered in light of molecular flexibility during the conjugation step, and the availability of the conjugated molecule for its target (cell surface molecules and the like.) Longer linkers may thus improve the biological activity of the compositions of the present invention, as well as the ease of preparation of them. The geometry of the linker may be used to orient a molecule for optimal reaction with a target. A linker with flexible geometry may allow the cross-linked polypeptides to conformationally adapt as they bind other polypeptides. The nature of the linker may be altered for various purposes. For example, the aryl-structure of MBuS was found less immunogenic than the aromatic spacer of MBS. Furthermore, the hydrophobicity and functionality of the linker molecules may be controlled by the physical properties of component molecules. For example, the hydrophobicity of a polymeric linker may be controlled by the order of monomeric units along the polymer, e.g. a block polymer in which there is a block of hydrophobic monomers interspersed with a block of hydrophilic monomers.

The chemistry of preparing and utilizing a wide variety of molecular linkers is well-known in the art and many pre-made linkers for use in conjugating molecules are commercially available from vendors such as Pierce Chemical Co., Roche Molecular Biochemicals, United States Biological, and the like.

3. Methods of Using the Engineered Antibody-Stress Protein Fusion Polypeptides and Compositions Suitable Therefor The engineered antibody-stress protein fusion polypeptides described herein can be administered to a subject to enhance that subject's immune response, particularly a cell-mediated cytolytic response, against a cell expressing an antigen against which the engineered antibody domains of the fusion polypeptide are directed. The fusion polypeptide may simply enhance the immune response (thus serving as an immunogenic composition), or confer protective immunity (thus serving as a vaccine).

Thus, the engineered antibody-stress protein fusion polypeptides produced as described above may be purified to a suitable purity for use as a pharmaceutical composition. Generally, a purified composition will have one species that comprises more than about 85 percent of all species present in the composition, more than about 85%, 90%, 95%, 99% or more of all species present. The object species may be purified to essential homogeneity (contaminant species cannot be detected in the composition by conventional detection methods) wherein the composition consists essentially of a single species. A skilled artisan may purify an engineered antibody-stress protein fusion polypeptide using standard techniques for protein purification, for example, immunoaffinity chromotography, size exclusion chromatography, etc. in light of the teachings herein. Purity of a polypeptide may be determined by a number of methods known to those of skill in the art, including for example, amino-terminal amino acid sequence analysis, gel electrophoresis and mass-spectrometry analysis.

Accordingly, provided are pharmaceutical compositions comprising the above-described engineered antibody-stress protein fusion polypeptides. In one aspect, provided are pharmaceutically acceptable compositions which comprise a therapeutically-effective amount of one or more of the compounds described above, formulated together with one or more pharmaceutically acceptable carriers (additives) and/or diluents. In another aspect, in certain embodiments, the compounds may be administered as such or in admixtures with pharmaceutically acceptable carriers and may also be administered in conjunction with other agents. Conjunctive (combination) therapy thus includes sequential, simultaneous and separate, or co-administration of the active compound in a way that the therapeutic effects of the first administered one has not entirely disappeared when the subsequent is administered.

The engineered antibody-stress protein fusion polypeptides described herein can be administered to a subject in a variety of ways. The routes of administration include intradermal, transdermal (e.g., slow release polymers), intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition, the compositions described herein can contain and be administered together with other pharmacologically acceptable components such as biologically active agents (e.g., adjuvants such as alum), surfactants (e.g., glycerides), excipients (e.g., lactose), carriers, diluents and vehicles. Furthermore, the compositions can be used ex vivo as a means of stimulating white blood cells obtained from a subject to elicit, expand and propagate antigen-specific immune cells in vitro that are subsequently reintroduced into the subject.

Further, an engineered antibody-stress protein fusion polypeptide can be administered by in vivo expression of a nucleic acid encoding such protein sequences into a human subject. Expression of such a nucleic acid can also be achieved ex vivo as a means of stimulating white blood cells obtained from a subject to elicit, expand and propagate antigen-specific immune cells in vitro that are subsequently reintroduced into the subject. Expression vectors suitable for directing the expression of engineered antibody-stress protein fusion polypeptides can be selected from the large variety of vectors currently used in the field. Preferred will be vectors that are capable of producing high levels of expression as well as are effective in transducing a gene of interest. For example, recombinant adenovirus vector pJM17 (All et al., *Gene Therapy* 1:367-84 (1994); Berkner K. L., *Biotechniques* 6:616-24 1988), second generation adenovirus vectors DE1/DE4 (Wang and Finer, *Nature Medicine* 2:714-6 (1996)), or adeno-associated viral vector AAV/Neo (Muro-Cacho et al., *J. Immunotherapy* 11:231-7 (1992)) can be used. Furthermore, recombinant retroviral vectors MFG (Jaffee et al., *Cancer Res.* 53:2221-6 (1993)) or LN, LNSX, LNCX, LXSN (Miller and Rosman, *Biotechniques* 7:980-9 (1989)) can be employed. Herpes simplex virus-based vectors such as pHSV1 (Geller et al., *Proc. Nat'l Acad. Sci.* 87:8950-4 (1990) or vaccinia viral vectors such as MVA (Sutter and Moss. *Proc. Nat'l Acad. Sci.* 89:10847-51 (1992)) can serve as alternatives.

Frequently used specific expression units including promoter and 3' sequences are those found in plasmid CDNA3 (Invitrogen), plasmid AHS, pRC/CMV (Invitrogen), pCMU II (Paabo et al., *EMBO J.* 5:1921-1927 (1986)), pZip-Neo SV (Cepko et al., *Cell* 37:1053-1062 (1984)) and pSRa (DNAX, Palo Alto, Calif.). The introduction of genes into expression units and/or vectors can be accomplished using genetic engineering techniques, as described in manuals like Molecular Cloning and Current Protocols in Molecular Biology (Sambrook, J., et al., Molecular Cloning, Cold Spring Harbor Press (1989); Ausubel, F. M. et al., Current Protocols in Molecular Biology, Greene Publishing Associates and Wiley-Interscience (1989)). A resulting expressible nucleic acid can be introduced into cells of a human subject by any method capable of placing the nucleic acid into cells in an expressible form, for example as part of a viral vector such as described above, as naked plasmid or other DNA, or encapsulated in targeted liposomes or in erythrocyte ghosts (Friedman, T., *Science*, 244:1275-1281 (1989); Rabinovich, N. R. et al., *Science*. 265:1401-1404 (1994)). Methods of transduction include direct injection into tissues and tumors, liposomal transfection (Fraley et al., *Nature* 370:111-117 (1980)), receptor-mediated endocytosis (Zatloukal et al., *Ann. N.Y. Acad. Sci.* 660:136-153 (1992)), and particle bombardment-mediated gene transfer (Eisenbraun et al., *DNA & Cell. Biol.* 12:791-797 (1993)).

The amount of engineered antibody-stress protein fusion polypeptide (fused, conjugated or noncovalently joined as discussed before) in the compositions of the present invention is an amount which produces an effective immunostimulatory response in a subject. An effective amount is an amount such that when administered, it induces an immune response. In addition, the amount of engineered antibody-stress protein fusion polypeptide administered to the subject will vary depending on a variety of factors, including the engineered antibody and stress protein employed, the size, age, body weight, general health, sex, and diet of the subject as well as on its general immunological responsiveness. Adjustment and manipulation of established dose ranges are well within the ability of those skilled in the art. For example, the amount of engineered antibody-stress protein fusion polypeptide can be from about 1 microgram to about 1 gram, preferably from about 100 microgram to about 1 gram, and from about 1 milligram to about 1 gram. An effective amount of a composition comprising an expression vector is an amount such that when administered, it induces an immune response against the antigen against which the engineered antibody is directed. Furthermore, the amount of expression vector administered to the subject will vary depending on a variety of factors, including the engineered antibody and stress protein expressed, the size, age, body weight, general health, sex, and diet of the subject, as well as on its general immunological responsiveness. Additional factors that need to be considered are the route of application and the type of vector used. For example, when prophylactic or therapeutic treatment is carried out with a viral vector containing a nucleic acid encoding an engineered antibody-stress protein fusion polypeptide, the effective amount will be in the range of $10^4$ to $10^{12}$ helper-free, replication-defective virus per kg body weight, preferably in the range of $10^5$ to $10^{11}$ virus per kg body weight and most preferably in the range of $10^6$ to $10^{10}$ virus per kg body weight.

Determination of an effective amount of fusion polypeptide for inducing an immune response in a subject is well within the capabilities of those skilled in the art, especially in light of the detailed disclosure provided herein.

An effective dose can be estimated initially from in vitro assays. For example, a dose can be formulated in animal models to achieve an induction of an immune response using techniques that are well known in the art. One having ordinary skill in the art could readily optimize administration to humans based on animal data. Dosage amount and interval may be adjusted individually. For example, when used as a vaccine, the polypeptides and/or strains of the invention may be administered in about 1 to 3 doses for a 1-36 week period. Preferably, 3 doses are administered, at intervals of about 3-4 months, and booster vaccinations may be given periodically thereafter. Alternate protocols may be appropriate for individual patients. A suitable dose is an amount of polypeptide or strain that, when administered as described above, is capable of raising an immune response in an immunized patient sufficient to protect the patient from the condition or infection for at least 1-2 years.

The compositions may also include adjuvants to enhance immune responses. In addition, such proteins may be further suspended in an oil emulsion to cause a slower release of the proteins in vivo upon injection. The optimal ratios of each component in the formulation may be determined by techniques well known to those skilled in the art.

Any of a variety of adjuvants may be employed in the vaccines of this invention to enhance the immune response. Most adjuvants contain a substance designed to protect the antigen from rapid catabolism, such as aluminum hydroxide or mineral oil, and a specific or nonspecific stimulator of immune responses, such as lipid A, or *Bortadella pertussis*. Suitable adjuvants are commercially available and include, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A, quil A, SBAS lc, SBAS2 (Ling et al., 1997, Vaccine 15:1562-1567), SBAS7, $Al(OH)_3$ and CpG oligonucleotide (WO96/02555).

In the vaccines of the present invention, the adjuvant may induce a Th1 type immune response. Suitable adjuvant systems include, for example, a combination of monophosphoryl lipid A, preferably 3-de-O-acylated monophosphoryl lipid A (3D-MPL) together with an aluminum salt. An enhanced system involves the combination of a monophosphoryl lipid A and a saponin derivative, particularly the combination of 3D-MLP and the saponin QS21 as disclosed in WO 94/00153, or a less reactogenic composition where the QS21 is quenched with cholesterol as disclosed in WO 96/33739. Previous experiments have demonstrated a clear synergistic effect of combinations of 3D-MLP and QS21 in the induction of both humoral and Th1 type cellular immune responses. A particularly potent adjuvant formation involving QS21, 3D-MLP and tocopherol in an oil-in-water emulsion is described in WO 95/17210 and may comprise a formulation.

4. Kits

The present invention provides kits for expressing an engineered antibody-stress protein fusion polypeptide. Such kits may be comprised of nucleic acids encoding an engineered antibody-stress protein fusion polypeptide. The nucleic acids may be included in a plasmid or a vector, e.g., a bacterial plasmid or viral vector. Other kits comprise an engineered antibody-stress protein fusion polypeptide. Furthermore, the present invention provides kits for producing and/or purifying an engineered antibody-stress protein fusion polypeptide.

The present invention provides kits for preventing or treating infectious, inflammatory, autoimmune or malignant disease in a patient. For example, a kit may comprise one or more pharmaceutical compositions as described above and optionally instructions for their use. In still other embodiments, the invention provides kits comprising one more pharmaceutical composition and one or more devices for accomplishing administration of such compositions.

Kit components may be packaged for either manual or partially or wholly automated practice of the foregoing methods. In other embodiments involving kits, instructions for their use may be provided.

EXEMPLIFICATION

The invention now being generally described, it will be more readily understood by reference to the following examples which are included merely for purposes of illustration of certain aspects and embodiments of the present invention, and are not intended to limit the invention in any way.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

Example 1

Construction of a Mab-HSP70 Conjugate and Immunization Using the Conjugate

A 14 amino acid long MISR2 peptide (SEQ ID NO 3: NANYSHLPPSGNRG) was chosen on the account of its stability, hydrophilicity and similarity with mouse MISR2. The peptide was conjugated with HSP70 using 25% glutaraldehyde. A Balb/c mouse was immunized twice with 2-weeks interval into foot pads at 100 µg of MISR peptide-HSP70 conjugate. The immune lymph node cells were fused with sp2/0 myeloma cells. The supernatant were screened by indirect ELISA using MISR peptide or MISR—HSP70 fusion protein or pure HSP70. The positives were cloned 2-4 times and propagated in mouse for ascites.

Figure 3:
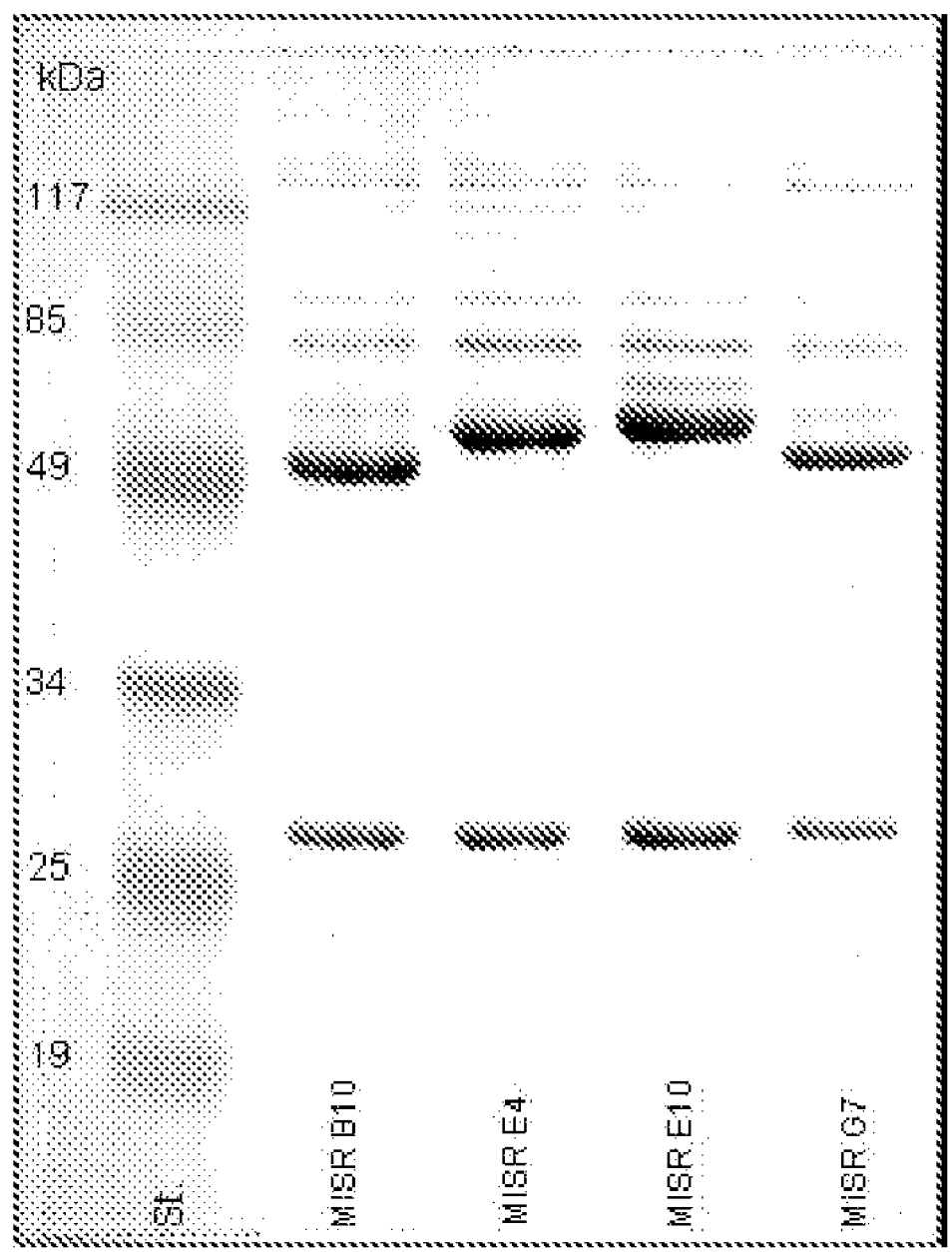
FIG. 3 depicts the results of 12% PAAG as described in Example 1, all proteins loaded at 4 µg/track under denaturing (DTT) condition.
Figure 5:
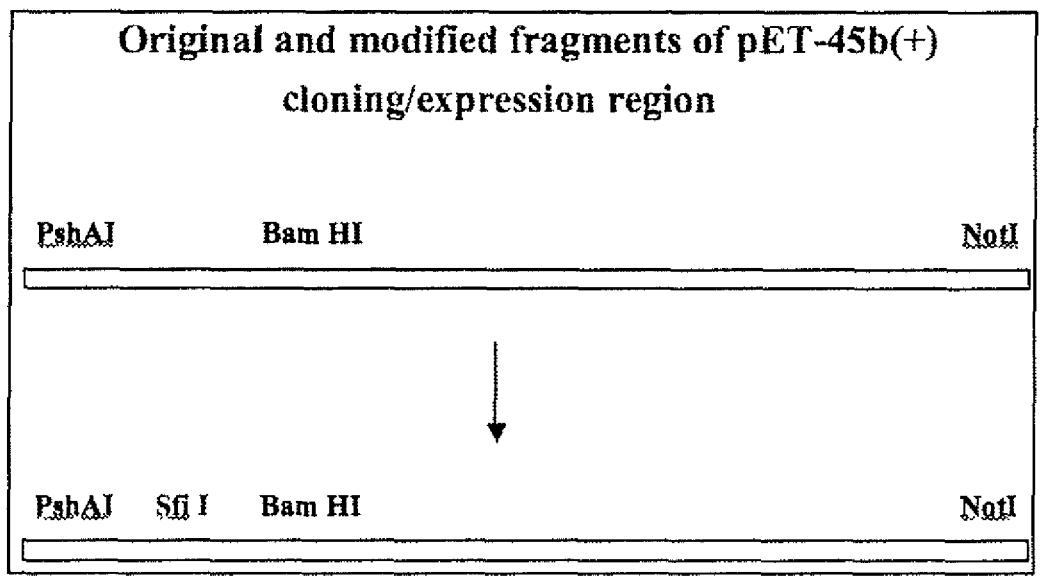
FIG. 5 illustrates modification of the pET-45b(+) expression vector. Schematic of the insertion of the SfiI restriction site.
Figure 6:
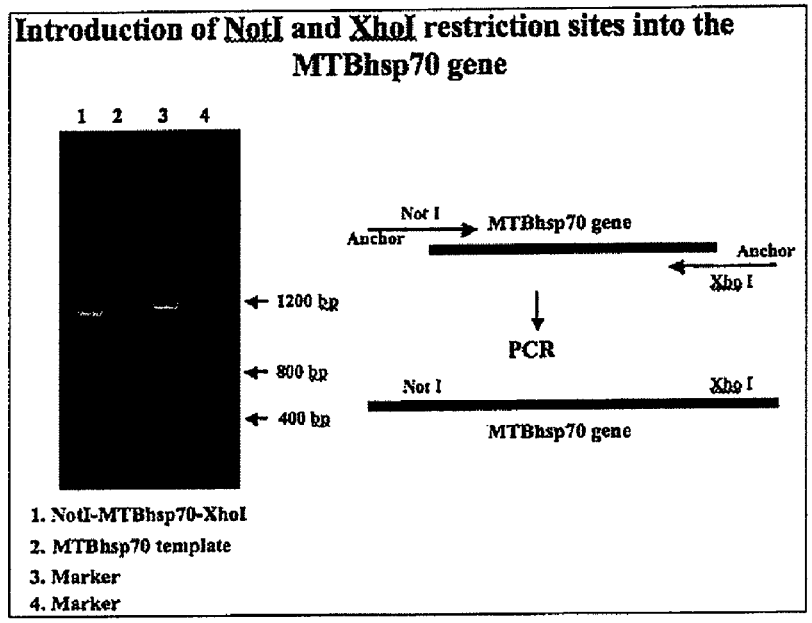
FIG. 6 shows introduction of NotI and XhoI restriction sites into MTBhsp70. Using primers overlapping the N- and C-terminals of MTBhsp70 a NotI site and an XhoI site were introduced by PCR. The resulting PCR product is shown in lane 1.
Figure 7:
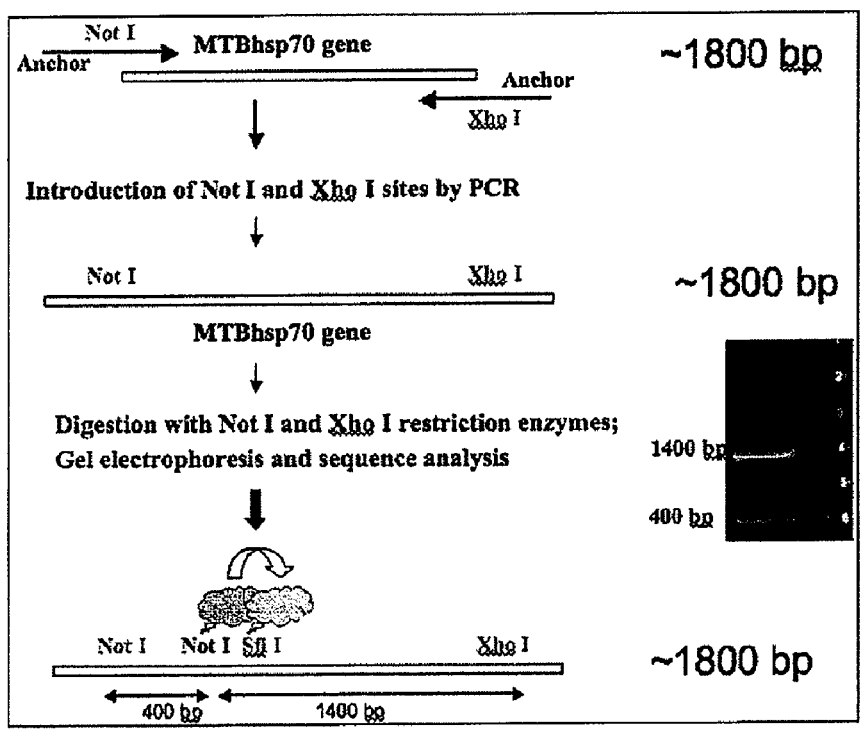
FIG. 7 shows digestion of the amplified MTBhsp70 with NotI and XhoI yielding 2 bands as shown on the gel picture. Sequencing analyses established the presence of internal NotI and SfiI sites.
Figure 8:
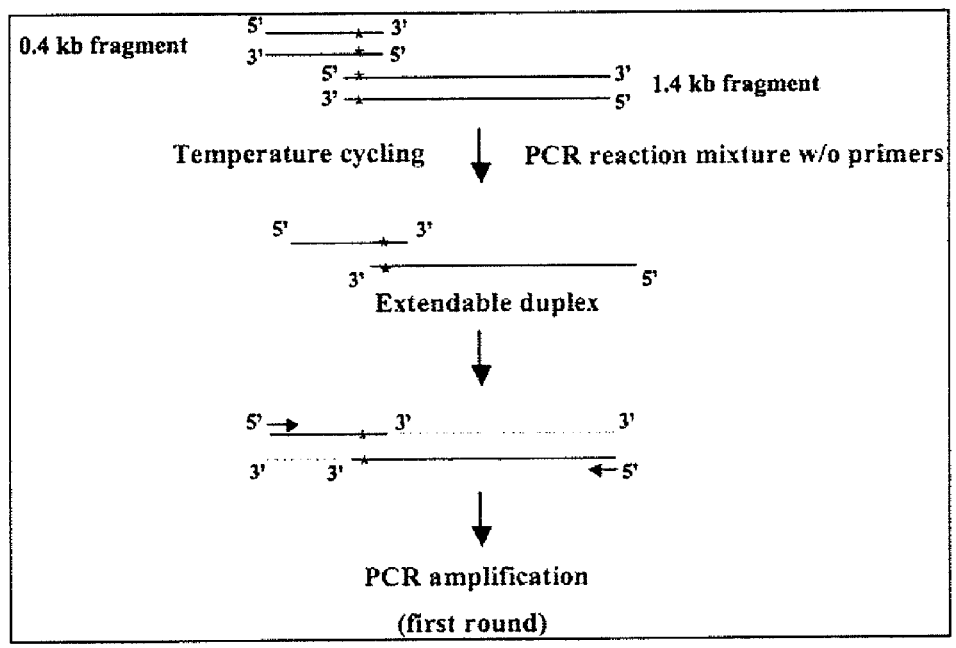
FIG. 8 shows removal of NotI and SfiI sites by using PCR based site directed mutagenesis. Using modified primers containing the desired mutations, two overlapping PCR products were generated. These were extended by PCR in absence of primers followed by the addition of specific primers.
Figure 9:
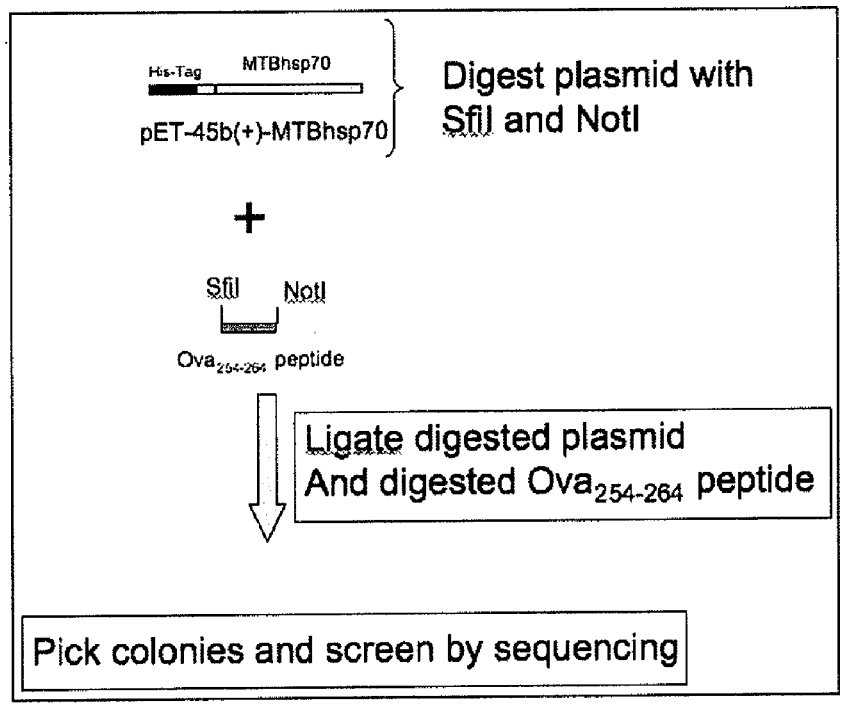
FIG. 9 shows introduction of the Ovalbumin peptide (residues 254-264) at the N-terminal of MTBhsp70. A synthetic linker coding for the Ovalbumin peptide SIINFEKL was digested with SfiI and NotI. A pET-45b(+) MTBhsp70 plasmid was cut with SfiI and NotI. Both components were ligated and the ligation product was used to transform competent bacteria. Ampicilin resistant colonies were picked and screened by sequencing.

The antibodies were purified from ascitic fluids by double salt-precipitation using ammonium sulphate. The antibodies were tested in PAAG electrophoresis under denaturing condition (FIG. 3). The antibodies were tested in indirect ELISA for binding with MISR—HSP70 conjugate, MISR peptide or HSP70. The results are shown in FIG. 4.

Prophetic Example #1

Tandab Comprising scFv and HSP70

FIG. 1 depicts an exemplary engineered antibody-stress protein fusion polypeptide comprising a tetravalent Tandab (engineered antibody) and HSP70 (stress protein). Tetravalent Tandabs may be prepared substantially as described in WO 99/57150, US20050089519 and Kipriyanov, et al., 1999, *J. Mol. Biol.* 293:41-56, all of which references are expressly incorporated herein by reference. Briefly, the construct encoding the single chain molecule comprising four antibody variable domains may additionally incorporate a stress protein gene, for example, HSP70. Alternatively, the single chain molecule comprising four antibody variable domains may be produced separately and then linked, e.g. covalently linked, to a stress protein such as HSP70.

Prophetic Example #2

Production of scFv in *E. coli*

*E. coli* strain GX6712 (F galk2 rspL c1857) and plasmid pGX8773 may be obtained from Genexcorp (Gaithersburg, Md.). The expression vector pGX8773 successfully encodes a single chain antibody construct, fused to the OmpA signal sequence, and contains an interdomain linker. The linker is the flexible linker peptide of *Trichoderma reesi*. Expression vector pLY3 encodes the scFV VH and VL genes fused to the OmpA signal sequence, with the VH and VL domains tethered by the linker. Expression vectors utilize a hybrid OL/PR lamba promoter with protein expression initiated by a temperature shift from 30° C. to 42° C. in *E. coli* GX6712. (Mallender & Voss, *J. Biol. Chem.* (1994) 269:199-206)

The scFv may be expressed and then tethered to HSP70 separately, or the scFv may be incorporated into a fusion polypeptide, as described throughout the specification and in Example 3 below.

Prophetic Example #3

Production of *Mycobacterium tuberculosis* HSP 70-scFv fusion in *E. coli*

A fusion of *Mycobacterium tuberculosis* HSP 70 with a scFv may be produced in *E. coli* as follows:

I. Characteristics of the *E. coli* Strain Producing Proteins scFv and DnaK (HSP70) *M. tuberculosis*.

The *E. coli* strain DLT 1270 was generated from DH 10A by virtue of integration of the gene lac 1 into the chromosome with D1-transduction. The genotype of DH 10A was as follows: DH 10B (ara D139 Δ (ara, leu) 7697 Δ (lac)X74 galU galK rpsL deoR φ80lacZ DM15 endA1 nupG recA1 mcrA Δ

(mrr hsdRMS mcrAN)). For a reference to DH 10B, see Grant, S., G., et al. *Proc. Natl. Acad. Sci. USA* (1990) 87:4645-4649.

II. Characteristics of the Plasmid

As a vector, the plasmid "QIAGEN" pQE-30 ("QIAGEN" Product Guide, www.qiagen.com) may be used.

III. Cloning of the Sequence of the scFv Gene of Interest in the Recombinant Vector dnaK For cloning, a previously obtained vector pQE30-dnaK-Y may be used. The recombinant plasmid pQE30-E711-dnaK produces the hybrid protein 6HIS-E7(type 11)-dnaK by allowing expression of the protein dnaK fused with a sequence 6HIS at the N-terminus Recombinant products with correct orientation have been identified using a restriction analysis. The scFv gene of interest (e.g., from vector pGX8773 described above and/or amplified using PCR) may be excised from the source by restriction digest and cloned at the BamHI site with pQE30-dnaK-Y plasmid.

IV. Protocol for the Cultivation of the Strain Producing Proteins scFv and DnaK (HSP70) *M. tuberculosis*.

For the cultivation, the nutrient medium Luria-Bertani (LB) may be prepared in distilled water and its pH adjusted to 7.5 with NaOH or citric acid. The media should be sterilized in an autoclave at 1 atm for 40 min. When the medium has cooled down to 40° C., ampicillin may be added aseptically to a final concentration of 50 μg/mL. The media with agar may be aseptically transferred to a Petri dish.

The producing strain may then be added to the freshly prepared media LB with agar. The Petri dish may be placed in a thermostat and incubated at 37° C. overnight to allow the culture to grow. For the preparation of the night culture, a desired amount of the LB media may be prepared in a conical flask. The media is transferred to the thermally resistant conical flasks so that the amount does not exceed ¼ of the flasks' volume. An isolated colony of *E. coli* may be transferred from the Petri dish and seeded in the conical flask. The flasks are placed in a thermoshaker and incubated overnight at 37° C. at 50 rev/min.

V. Fermentation of DLT1270-pQE30-scFv-dnaK

Synthesis of the hybrid peptide scFv-DnaK may be induced by adding IPTG to the culture. The overnight culture DLT1270/pQE30-scFv-DnaK, grown in LB-media, may be diluted 1:100 and grown in a LB-media to OD600=0.5. 0.1 mM IPTG is added and cultivation continued for 3 h. The density of the culture may be measured using a spectrophotometer. After the end of fermentation, the biomass may be collected by centrifugation at 3000×G for 15 minutes at 4° C. Generation of the protein may be followed by electrophoresis in polyacrylamide gel.

Example 4

Production of MTBhsp70

MTBhsp70 was subcloned into the expression vector pET45b(+) by first modifying the vector to introduce the desired restriction site SfiI. This modification allows introduction of the MTBhsp70 protein at the NotI/XhoI site and other proteins such as scFvs, antigens, etc. at the SfiI/NotI site (FIG. 5). This particular approach can be modified to introduce the desired proteins at the C-terminal of MTBhsp70. Using the MTBhsp70 plasmid provided by Dr. Richard Young, restriction sites NotI and XhoI were introduced at the 5' and 3' end respectively (FIG. 6).

Digestion of the amplified MTBhsp70 fragment shown in lane 1 of FIG. 2 with the restriction enzymes NotI and XhoI unexpectedly revealed 2 bands (FIG. 7). Sequencing analyses revealed that MTBhsp70 contains internal NotI and SfiI restriction sites. These were removed using the strategy depicted in FIG. 8. The resulting MTBhsp70 pET-45b(+) construct was then used to transform competent BL21(DE3) bacteria. Expression of MTBhsp70 was induced by adding 1 mM IPTG. Cells were grown in LB medium at 37° C. to an $OD_{600}$ of 0.5. Cells were spun down and suspended in LB medium containing 1 mM IPTG and growth continued for 4 hours at the indicated temperature. Cells were fractionated and aliquots were run on SDS-PAGE and proteins were stained with Coomassie Blue. When induced cells were grown at 37° C. the majority of the MTBhsp70 protein was found in insoluble inclusion bodies. By reducing the growth temperature post induction to 30° C., large amounts of soluble MTBhsp70 were produced. The MTBhsp70 protein found in the soluble and periplasmic fractions of BL21(DE3) grown at 30° C. was successfully purified by metal affinity chromatography (MAC) using Cobalt spin columns. Cells were grown at 37° C. to an $OD_{600}$ of 0.5 and then spun down. Cells were suspended in growth media containing 1 mM IPTG and allowed to grow for 4 hours at 30° C. Cells were fractionated according to standard methods consisting of solubilization with B-PER reagent from Pierce.

Example 5

Production of MTBhsp70-fusion proteins

In order to demonstrate the immunostimulatory properties of MTBhsp70-fusion proteins, an Ovalbumin peptide-MTBhsp70 and two scFv-MTBhsp70 fusion products were constructed.

L Ova-257-264-MTBhsp 70 fusion protein. Ovalbumin's immunodominant peptide consisting of residues 257-264 (SIINFEKL) was fused to the N-terminal region of MTBhsp70 by digesting the MTBhsp70 pET-45b(+) plasmid with SfiI and NotI and introducing a linker coding for the immunodominant peptide that is also digested with SfiI and NotI (FIG. 9). Upon ligation, a number of colonies were obtained, and their identities were confirmed by sequencing. As observed with MTBhsp70, induction of Ova-257-264-MTBhsp70 is optimum when the growth temperature, post-IPTG induction, is kept at 30° C. Successful expression of Ova254-264-MTBhsp70 was obtained in the soluble fraction of BL21(DE3).

II. scFv-MTBhsp70 fusion proteins. scFvs were fused to the N-terminal of MTBhsp70. A human combinatorial scFv phage display library was constructed and used it to select Ovalbumin specific scFvs. The other scFv, MOV18, is specific for the high affinity Folate Receptor expressed on ovarian cancer cells. The cloning method is similar to the approach used for the introduction of the $Ova_{254-264}$ peptide at the N-terminal of MTBhsp70. The SfiI/NotI scFv portion was purified from their respective plasmids followed by ligation into the SfiI/NotI digested expression vector MTBhsp70 pET-45b(+). The anti-Ovalbumin scFvs had several nonsense mutations that had to be removed by site directed mutagenesis. However, upon induction of bacteria carrying both constructs, it was found that induction with IPTG resulted in the fusion proteins being expressed in inclusion bodies.

Example 6

Generation of Single Chain Variable Fragments (scFV) Targeting New Antigen Linked to MTB HSP70

A Novel Fusion Vaccine

The generation of scFVs that bind to either known or uncharacterized antigens by "panning" against the desired antigen may be carried out as follows. The scFV is comprised of the antigen-binding domains of heavy $V_H$ and light $V_\kappa$ chains of antibodies, and can be made in E. coli. Repertoires of these scFV combinations can be built from the genes of heavy $V_H$ and light $V_\kappa$ chains obtained from B-lymphocytes either before or after immunization, or from the V-gene segments that have been cloned and rearranged in vitro. These gene segments can be combinatorially cloned into an appropriate phagemid vector to generate an scFv library that can be used to transform E. coli. Infection of these transformed bacteria with a suitable helper phage results in the production of recombinant phages expressing scFvs on their surface. Using successive rounds of selection (panning) it is possible to enrich the population of phage expressing scFvs with binding affinities to a particular antigen. One can derive scFV's from naive or non-immunized human lymphocytes, by combining elements of both immunized and non-immunized lymphocytes, or by various combinations of the above with a synthetic antibody library generated through the introduction of randomized sequences in the antibody binding site. This method has been used to rapidly generate scFV's against highly dangerous pathogens such as SARS-associated coronavirus (SARS-Cov). The use of human B cells as the source the V-gene segments has also eliminated the antigenicity of scFV's.

The approach described herein may be used for targeting antigens whose sequence may not be known or structure even identified. In place of directly linking synthetic antigen peptides to MTb HSP 70 to generate a vaccine, instead scFV's may be linked to MTb HSP 70 to develop a novel fusion protein vaccine for presenting antigen to APCs in order to generate both a humoral and CD-8 response. The scFV's can be selected for their binding to an uncharacterized antigen or to a characterized antigen by binding studies, and the appropriate V-genes can then be selected. The scFV genes are fused to the gene for MTb HSP 70, and the new fusion gene is expressed as the fusion protein in E. coli. This has already been successfully done, using the scFV for cholera toxin subunit B bound to MTb HSP 70. This scFV-MTb HSP 70 fusion protein bound to antigen with a binding affinity of approximately $10^{-9}$ M.

Example 7

Rapid Assembly of Novel Vaccine Using Pre-formed MTb-HSP 70 with Linkers for scFvs Through unique cloning strategies, large amounts of pure MTb HSP 70 may be expressed with great efficiency. The scFV-MTb HSP 70 fusion vaccine may be produced by cloning the individual scFV sequence, a linker sequence, and the MTb HSP 70 sequence into a phagemid vector for expression of the entire fusion vaccine in E. coli. A fast method may be used for generating a new fusion vaccine in which previously produced (potentially GMP) MTb HSP 70 with a linker that preferentially binds to scFvs could be stockpiled, and then rapidly coupled to newly produced scFV's. This would dramatically reduce the complexity and time of generating a new vaccine. Protein L from Peptostreptococcus magnus preferentially binds to the backbone of the variable region of light chains, leaving the antigen combining site unobstructed. The gene coding for Protein L could be cloned into the plasmid coding the gene for MTb HSP 70 in order to create a fusion of Protein L (PL) and MTb HSP 70. Large amounts of this new fusion protein could be grown in advance and stored. When needed, appropriate scFV's could be generated quickly, and stoichiometrically mixed with preformed PL-MTb HSP 70 fusion, creating the newly targeted scFv-PL-MTb HSP 70 fusion vaccine.

An even simpler chemical technique that binds scFV's and Fab's as a chemical linker may be used to further facilitate the process. Thus, the MTB HSP 70 fusion subunit, the MTb HSP 70-linker subunit, and scFV's may be produced. An scFv-linker MTB HSP 70 fusion vaccine may be produced. Thereafter small changes in the antigen recognition moiety of the new scFV to deal with new pathogens might be made.

I. Expression of the recombinant heat shock protein 70 from Mycobacterium tuberculosis (MTB hsp70). Our rapid vaccine development strategy relies on the availability of pure MTBhsp70 and the production of pure protein/peptide-MTBhsp70 fusions. This was accomplish by subcloning MTBhsp70 from the pKS1 this vector obtained from Dr. Richard Young at the Massachusetts Institute of Technology into the expression vector pET45b(+) (Novagen). This vector is particularly useful as it adds a polyhistidine-tag at the N-terminal of the construct thus facilitating protein purification by Nickel or Cobalt affinity chromatography. Furthermore, upon purification, the polyhistidine-tag can be removed by enterokinase digestion. Our strategy consisted of modifying the vector such that an scFv-MTBhsp70 fusion construct could be obtained by taking advantage of the fact that scFvs contain unique SfiI/NotI restriction sites. We first modified pET45b(+) by introducing unique SfiI and NotI sites and subcloning MTBhsp70 into the NotI/XhoI site of the modified vector. The Modified pET45b(+) expression vector allows the insertion of scFv or protein or peptide antigens in the SfiI/NotI cloning region. An enterokinase recognition site is located at the junction between PshAI and SfiI.

BL21 (DE3) cells were transformed with our modified vector and production of soluble MTBhsp70 may be induced upon addition of IPTG to the growth media. Passage of the soluble cell extract over a Cobalt affinity matrix yielded essentially pure MTBhsp70.

II. Making human scFv (single strain variable fragment) phage display library from peripheral lymphocytes of unimmunized donors. Total RNA was prepared from peripheral blood lymphocytes (PBLs) of unimmunized donors using Ambion's Tri Reagent. PBLs were separated from red blood cells by centrifugation through Ficoll-Hypaque, recovered and washed twice with PBS. 1 ml of Tri Reagent per $10 \times 10^6$ PBLs. We typically observed yields of 50 to 70 micrograms of RNA per 18 ml of blood collected in EDTA coated tubes.

Primer design. Primers originally described by Gregory Winter were used (Marks J D, Hoogenboom H R, Bonnert T P, McCafferty J, Griffiths A D, Winter G. By-passing immunization. Human antibodies from V-gene libraries displayed on phage. J Mol Biol 1991; 222581-97.). The forward primers were designed to match each member of the human V-gene families, and reverse primers were designed to match of the human germ line J segments. In addition, sets of PCR primers were designed to optimize the random linking of $V_H$ segments to $V_K$ or $V_\lambda$ gene segments. Finally, a set of primers containing the desired restriction sites SfiI and NotI was used to reamplify the scFv gene repertoire to allow cloning into the vector pCANTAB5E.

First-strand cDNA synthesis and Amplification of VHg, VHm, Vl and Vk. Four first-strand cDNAs were synthesized from total RNA (SuperScript111 enzyme, Invitrogen) using either IgG or IgM constant region-specific primer for the heavy chains, or light chain κ or λ. constant region-specific primers. These cDNAs were used to generate 4 separate repertoires of scFv genes ($V_H\mu$-Vκ, $V_H\mu$-Vλ, $V_H$Y-Vκ, and $V_H$Y-Vλ).

Making scFv linker DNA. To make the scFv linker DNA, 52 separate PCR reactions were performed using each of the 4 forward J-segment-specific primers from heavy chain in combination with each of the 13 reverse Vκ and Vλ specific primers. The rearranged $V_H$ and $V_L$ PCR products were combined with linker DNA overlapping the C termini of $V_H$ and the N termini of $V_L$ gene segments and subjected to PCR amplification. The resulting scFv gene repertoires were subsequently amplified with primers containing SfiI and NotI restriction sites. The amplified scFv gene repertoires (IgG-$V_L$ and IgM-$V_L$ repertoires) were digested with SfiI and NotI restriction enzymes and ligated into the similarly digested phagemid vector pCANTAB 5E. The ligated scFvs were used to transform electrocompetent TG1 cells to yield a library of approximately $1 \times 10^6$ clones. Addition of CT helper phage to the transformed TG1 cells yielded the scFvs phage library used for screening.

Construction of CT Helper phage. In order to minimize the production of undesired helper phage, we constructed the infection deficient CT helper phage described by Kramer (Kramer, R. A., et al., *Nucl. Acid Res.* 2003, 31, 2-9). In order to rescue the phage library, the CT-phage genome is packaged in a phage envelope containing a functional gene 3. This was accomplished by transforming electrocompetent XLI-Blue cells carrying the fully functional gene 3 on pUC19.

Non-chemical conjugation of target specific immunoglobulins to MTBhsp70. To take advantage of the availability of monoclonal antibodies directed against antigens of interest for vaccine development we intend to clone the immunoglobulin binding region from *Peptostreptococcus Magnus* Protein L (PpL) into the SfiI/NotI site of MTBhsp70 pET45b(+) vector. PpL is a 719 amino acids protein with a series of 4 to 5 immunoglobulin light chain binding repeated binding region (B1-B5) (Kastern W, Sjobring U, Bjorck L. Structure of peptostreptococcal protein L and identification of a repeated immunoglobulin light chain-binding domain. *J Biol Chem* 1992; 267:12820-5.). The B1-B5 repeated region of PpL may be amplified from EcoRI digested P. Magnus genomic DNA using primers LP1 and LP2 modified to include the SfiI and NotI restriction sites respectively (Kastern, Sjobring et al. 1992). This novel construct will take advantage the light chain binding activity of proteinL without interfering with the antigen binding property of the bound immunoglobulin. Conjugation of a PpL affinity ligand mimic to MTBhsp70. An affinity ligand that mimics the immunoglobulin binding properties of protein L may be prepared as described by Lowe (Roque A C, Taipa M A, Lowe C R. An artificial protein L for the purification of immunoglobulins and fab fragments by affinity chromatography. *J Chromatogr A* 2005; 1064:157-67.). A stable conjugate that could be used to bind scFv and behave similarly to protein L may be generated.

Equivalents

The present invention provides, among other things, engineered antibody-stress protein fusion polypeptides. While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

REFERENCES

Incorporated by reference in their entirety are any polynucleotide and polypeptide sequences which reference an accession number correlating to an entry in the public database of the National Center for Biotechnology Information (NCBI). The contents of all cited references including literature references, issued patents, published or non published patent applications as cited throughout this application are hereby expressly incorporated by reference. Additionally, the following references are expressly incorporated herein by reference:

1. Hoogenboom H R. Selecting and screening recombinant antibody libraries. Nat Biotechnol 2005; 23:1105-16.
2. Marks J D, Hoogenboom H R, Bonnert T P, McCafferty J, Griffiths A D, Winter G. By-passing immunization. Human antibodies from V-gene libraries displayed on phage. J Mol Biol 1991; 222581-97.
3. Flego M, Di Bonito P, Ascione A, et al. Generation of human antibody fragments recognizing distinct epitopes of the nucleocapsid (N) SARSCoV protein using a phage display approach. BMC Infect Dis 2005; 5:73.
4. Duan J, Yan X, Guo X, et al. A human SARS-CoV neutralizing antibody against epitope on S2 protein. Biochem Biophys Res Commun 2005; 33311 86-93.
5. Zugel U, Kaufmann S H. Role of heat shock proteins in protection from and pathogenesis of infectious diseases. Clin Microbiol Rev 1999; 12: 19-39.
6. Srivastava P K, Maki R G. Stress-induced proteins in immune response to cancer. Curr Top Microbiol Immunol 1991; 167:109-23.
7. Chen W, Syldath U, Bellmann K, Burkart V, Kolb H. Human 60-kDa heatshock protein: a danger signal to the innate immune system. J Immunol 1999; 1621321 2-9.
8. Kastern W, Sjobring U, Bjorck L. Structure of peptostreptococcal protein L and identification of a repeated immunoglobulin light chain-binding domain. J Biol Chem 1992; 267:12820-5.
9. Roque A C, Taipa M A, Lowe C R. An artificial protein L for the purification of immunoglobulins and fab fragments by affinity chromatography. J Chromatogr A 2005; 1064:157-67.

The invention claimed is:

1. An isolated nucleic acid encoding a fusion polypeptide, wherein the fusion polypeptide comprises an engineered antibody and a stress protein.

2. The isolated nucleic acid of claim 1, wherein the engineered antibody comprises at least one scFv.

3. The isolated nucleic acid of claim 1, wherein the engineered antibody comprises at least one Fab fragment.

4. The isolated nucleic acid of claim 1, wherein the stress protein is HSP70.

5. The isolated nucleic acid of claim 4, wherein the stress protein is *Mycobacterium tuberculosis* HSP70.

6. The isolated nucleic acid of claim 4, wherein the stress protein is *Mycobacterium bovis* HSP70.

7. The isolated nucleic acid of claim 1, wherein the engineered antibody is multivalent.

8. The isolated nucleic acid of claim 7, wherein the multivalent engineered antibody is multispecific.

9. The isolated nucleic acid of claim 7, wherein the engineered antibody is tetravalent.

10. The isolated nucleic acid of claim 9, wherein the engineered antibody is a Tandab.

11. The isolated nucleic acid of claim 9, wherein the stress protein is HSP70.

12. The isolated nucleic acid of claim 11, wherein the stress protein is *Mycobacterium tuberculosis* HSP70.

13. The isolated nucleic acid of claim 11, wherein the stress protein is *Mycobacterium bovis* HSP70.

14. An expression vector comprising the nucleic acid of claim 1.

15. An expression vector of claim 14, which is a plasmid.

16. A host cell comprising the expression vector of claim 14.

17. A host cell of claim 16, which is a prokaryotic cell.

18. A host cell of claim 16, which is a eukaryotic cell.

19. A method of making a fusion protein comprising an engineered antibody and stress protein, comprising the step of culturing the host cell of claim 16 under appropriate conditions.

20. A method of making a fusion protein comprising an engineered antibody and stress protein, comprising the step of
    contacting the engineered antibody and the stress protein with a linker molecule, wherein the linker molecule comprises at least two functional groups that react with amine, carboxyl, or sulfhydryl groups.

* * * * *